(12) United States Patent
Bhalay et al.

(10) Patent No.: US 8,372,845 B2
(45) Date of Patent: Feb. 12, 2013

(54) PYRAZINE DERIVATIVES AS ENAC BLOCKERS

(75) Inventors: Gurdip Bhalay, Horsham (GB); Lee Edwards, Partridge Green (GB); Catherine Howsham, Horsham (GB); Peter Hunt, Storrington (GB); Nichola Smith, Angmering (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/232,175

(22) Filed: Sep. 14, 2011

(65) Prior Publication Data

US 2012/0071479 A1 Mar. 22, 2012

Related U.S. Application Data

(60) Provisional application No. 61/383,985, filed on Sep. 17, 2010, provisional application No. 61/524,495, filed on Aug. 17, 2011.

(51) Int. Cl.
*A61K 31/497* (2006.01)

(52) U.S. Cl. ............... 514/255.05; 514/255.06; 544/407

(58) Field of Classification Search .................. 544/407
See application file for complete search history.

(56) References Cited

FOREIGN PATENT DOCUMENTS

| WO | 2009/074575 A2 | 6/2009 |
| WO | 2009/150137 A2 | 12/2009 |
| WO | 2011/050325 A1 | 4/2011 |

OTHER PUBLICATIONS

Borisy et al. Systematic discovery of multicomponent therapeutics. 2003, Proceedings of the National Academy of Sciences of the United States of America. 100, 7977-7982.*
Pavlov et al. Regulation of ENaC-Mediated Sodium Reabsorption by Peroxisome Proliferator-Activated Receptors. 2010, PPAR Research, 2010, 1-9.*
Li et al.; "Stereoselective Blockade of Amphibian Epithelial Sodium Channels by Amiloride Analogs"; J. Pharm. and Exp. Ther.; 267(3):1081-1084 (1993).

* cited by examiner

*Primary Examiner* — Brian McDowell
(74) *Attorney, Agent, or Firm* — Joshua Roth

(57) ABSTRACT

Compounds of Formula I:

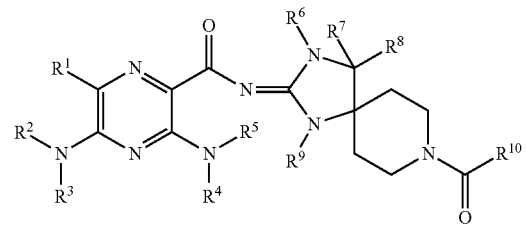

and pharmaceutically acceptable salts and solvates thereof, wherein $R^1$, $R^2$, $R^3$, $R^4$, $R^5$, $R^6$, $R^7$, $R^8$, $R^9$, and $R^{10}$ have the meanings as indicated in the specification, are useful for treating diseases mediated by blockade of the epithelial sodium channel. Pharmaceutical compositions that contain the compounds and processes for preparing the compounds are also described.

16 Claims, No Drawings

PYRAZINE DERIVATIVES AS ENAC BLOCKERS

RELATED APPLICATIONS

This application claims the benefit of U.S. Provisional Application No. 61/383,985, filed on Sep. 17, 2010, and U.S. Provisional Application No. 61/524,495, filed on Aug. 17, 2011, the entire teachings of which are incorporated by reference.

This invention relates to organic compounds and their use as pharmaceuticals, in particular for the treatment of inflammatory, obstructive or allergic diseases and conditions, particularly an inflammatory or obstructive airways disease or mucosal hydration.

In one aspect, the invention provides a compound of Formula I:

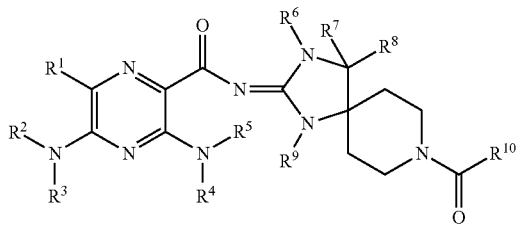

I or a pharmaceutically acceptable salt or solvate thereof, wherein $R^1$ is H, halogen, $C_1$-$C_8$-alkyl, $C_1$-$C_8$-haloalkyl, $C_1$-$C_8$-haloalkoxy, $C_3$-$C_{15}$-carbocyclic group, nitro, cyano, a $C_6$-$C_{15}$-membered aromatic carbocyclic group, or a $C_1$-$C_8$-alkyl substituted by a $C_6$-$C_{15}$-membered aromatic carbocyclic group;

$R^2$, $R^3$, $R^4$ and $R^5$ are each independently selected from H and $C_1$-$C_6$ alkyl;

$R^6$, $R^7$, $R^8$ and $R^9$ are each independently selected from H; $SO_2R^{16}$; aryl optionally substituted by one or more Z groups; a $C_3$-$C_{10}$ carbocyclic group optionally substituted by one or more Z groups; $C_3$-$C_{14}$ heterocyclic group optionally substituted by one or more Z groups; $C_1$-$C_8$ alkyl optionally substituted by an aryl group which is optionally substituted by one or more Z groups, a $C_3$-$C_{10}$ carbocyclic group optionally substituted by one or more Z groups or a $C_3$-$C_{14}$ heterocyclic group optionally substituted by one or more Z groups;

$R^{10}$ is represented by the formula 2:
—($C_0$-$C_3$alkylene)-B—X—($CR^{11a}R^{12a}$)$_m$—($CR^{11b}R^{12b}$)$_n$—($CR^{11c}R^{12c}$)$_p$—$C(O)OR^{13}$,
wherein the alkylene groups are optionally substituted by one or more Z groups;

B is aryl optionally substituted by one or more Z groups;

X is selected from a bond, —$NR^{15}(SO_2)$—, —$(SO_2)NR^{15}$—, —$(SO_2)$—, —$NR^{15}C(O)$—, —$C(O)NR^{15}$—, —$NR^{15}C(O)NR^{17}$—, —$NR^{15}C(O)O$—, —$NR^{15}$—, $C(O)O$, $OC(O)$, $C(O)$, $O$ and $S$;

$R^{11a}$, $R^{11b}$, $R^{11c}$, $R^{12a}$, $R^{12b}$ and $R^{12c}$ are each independently selected from H and $C_1$-$C_6$ alkyl; or $R^{11a}$ and $R^{12a}$ together with the carbon atom to which they are attached form a 3- to 8-membered cycloalkyl group; or $R^{11b}$ and $R^{12b}$ together with the carbon atom to which they are attached form a 3- to 8-membered cycloalkyl group; or $R^{11c}$ and $R^{12c}$ together with the carbon atom to which they are attached form a 3- to 8-membered cycloalkyl group;

$R^{13}$ is selected from ($C_1$-$C_3$ alkyl)-$C(O)NR^{22}R^{23}$; ($C_1$-$C_3$ alkyl)-$C(O)OR^{23}$; and ($C_1$-$C_3$ alkyl)-$NR^{23}C(O)R^{22}$ $R^{15}$ and $R^{17}$ are each independently selected from H and $C_1$-$C_6$ alkyl;

$R^{16}$ is selected from $C_1$-$C_8$ alkyl, aryl and a 3- to 14-membered heterocyclic group, the heterocyclic group including one or more heteroatoms selected from N, O and S;

Z is independently selected from —OH, aryl, —O-aryl, $C_7$-$C_{14}$ aralkyl, —O—$C_7$-$C_{14}$ aralkyl, $C_1$-$C_6$ alkyl, $C_1$-$C_6$ alkoxy, —$NR^{19}(SO_2)R^{21}$, —$(SO_2)NR^{19}R^{21}$, —$(SO_2)R^{20}$, —$NR^{19}C(O)R^{20}$, —$C(O)NR^{19}R^{20}$, —$NR^{19}C(O)NR^{26}R^{18}$, —$NR^{19}C(O)OR^{20}$, —$NR^{19}R^{21}$, $C(O)OR^{19}$, —$C(O)R^{19}$, $SR^{19}$, —$OR^{19}$, oxo, CN, $NO_2$, and halogen, wherein the alkyl, alkoxy, aralkyl and aryl groups are each optionally substituted by one or more substituents selected from OH, halogen, $C_1$-$C_4$ haloalkyl and $C_1$-$C_4$ alkoxy;

$R^{18}$, $R^{20}$ and $R^{22}$ are each independently selected from H and $C_1$-$C_6$ alkyl;

$R^{19}$, $R^{21}$ and $R^{23}$ are each independently selected from H; $C_1$-$C_8$ alkyl; $C_3$-$C_9$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and —$C(O)C_1$-$C_6$ alkyl; —($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl and —$C(O)C_1$-$C_6$ alkyl; wherein the alkyl groups are optionally substituted by one or more halogen atoms, hydroxyl, $C_1$-$C_4$ alkoxy, —$C(O)NH_2$, —$C(O)NHC_1$-$C_6$ alkyl or —$C(O)N(C_1$-$C_6$ alkyl$)_2$; or $R^{19}$ and $R^{20}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —$S(O)_2$-aryl; —$S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy; or $R^{19}$ and $R^{21}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —S(O)$_2$-aryl; —S(O)$_2$—C$_1$-C$_6$ alkyl; C$_1$-C$_6$ alkyl optionally substituted by one or more halogen atoms; C$_1$-C$_6$ alkoxy optionally substituted by one or more OH groups or C$_1$-C$_4$ alkoxy; and —C(O)OC$_1$-C$_6$ alkyl, wherein the aryl and heterocyclic substituent groups are themselves optionally substituted by C$_1$-C$_6$ alkyl, C$_1$-C$_6$ haloalkyl or C$_1$-C$_6$ alkoxy; or R$^{18}$ and R$^{20}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —S(O)$_2$-aryl; —S(O)$_2$—C$_1$-C$_6$ alkyl; C$_1$-C$_6$ alkyl optionally substituted by one or more halogen atoms; C$_1$-C$_6$ alkoxy optionally substituted by one or more OH groups or C$_1$-C$_4$ alkoxy; and —C(O)OC$_1$-C$_6$ alkyl, wherein the aryl and heterocyclic substituent groups are themselves optionally substituted by C$_1$-C$_6$ alkyl, C$_1$-C$_6$ haloalkyl or C$_1$-C$_6$ alkoxy; or R$^{22}$ and R$^{23}$ together with the atom(s) to which they are attached form a 5- to 10-membered heterocyclic group, the heterocyclic group including one or more further heteroatoms selected from N, O and S, the heterocyclic group being optionally substituted by one or more Z groups;

m is 0, 1, 2 or 3;
n is 0, 1, 2 or 3;
p is 0, 1, 2 or 3;
wherein at least one of m, n or p is not 0.

In another embodiment of the invention as defined anywhere above, R$^1$ is halogen.

In a further embodiment, R$^1$ is chlorine

In another embodiment of the invention as defined anywhere above, R$^2$, R$^3$, R$^4$ and R$^5$ are H.

In another embodiment of the invention as defined anywhere above, R$^6$, R$^7$, R$^8$ and R$^9$ are H.

In another embodiment of the invention as defined anywhere above, R$^{10}$ is —B—X—(CR$^{11a}$R$^{12a}$)—(CR$^{11b}$R$^{12b}$)—C(O)OR$^{13}$.

In a further embodiment, R$^{10}$ is —B—(SO$_2$)NR$^{15}$—(CR$^{11a}$R$^{12a}$)—(CR$^{11b}$R$^{12b}$)—C(O)OR$^{13}$.

In an alternative yet further embodiment, R$^{10}$ is —B—NR$^{15}$C(O)NR$^{17}$—(CR$^{11a}$R$^{12a}$)—(CR$^{11b}$R$^{12b}$)—C(O)OR$^{13}$.

In an alternative embodiment of the invention as defined anywhere above, R$^{10}$ is —(C$_2$alkylene)-B—X—(CR$^{11a}$R$^{12a}$)—C(O)OR$^{13}$, wherein the alkylene groups are optionally substituted by one or more Z groups. In a further embodiment, the alkylene groups are unsubstituted. In a yet further embodiment, X is O.

In a yet further embodiment, R$^{10}$ is —(CH$_2$)$_2$—B—O—(CR$^{11a}$R$^{12a}$)—C(O)OR$^{13}$.

In another embodiment of the invention as defined anywhere above, B is phenyl optionally substituted by one or more Z groups.

In a further embodiment B is phenyl optionally substituted by halogen; in a yet further embodiment the halogen is chlorine.

In another embodiment of the invention as defined anywhere above, X is selected from —(SO$_2$)NR$^{15}$—, —NR$^{15}$C(O)NR$^{17}$—, and O.

In another embodiment of the invention as defined anywhere above, R$^{15}$ and R$^{17}$ are H.

In another embodiment of the invention as defined anywhere above, R$^{11a}$, R$^{11b}$, R$^{11c}$, R$^{12a}$, R$^{12b}$ and R$^{12c}$ are each independently selected from H and C$_1$-C$_3$ alkyl; or R$^{11a}$ and R$^{12a}$ together with the carbon atom to which they are attached form a 3-, 4- or 5-membered cycloalkyl group; or R$^{11b}$ and R$^{12b}$ together with the carbon atom to which they are attached form a 3-, 4- or 5-membered cycloalkyl group; or R$^{11c}$ and R$^{12c}$ together with the carbon atom to which they are attached form a 3-, 4- or 5-membered cycloalkyl group.

In another embodiment of the invention as defined anywhere above, m is 0 or 1.

In another embodiment of the invention as defined anywhere above, n is 0 or 1.

In another embodiment of the invention as defined anywhere above, p is 0 or 1.

In another embodiment of the invention as defined anywhere above, the sum of m, n and p is 0, 1, 2, or 3; in a further embodiment the sum is 1, 2, or, 3; in a yet further embodiment, the sum is 1 or 2.

In another embodiment of the invention as defined anywhere above wherein X is selected from —(SO$_2$)NR$^{15}$— and —NR$^{15}$C(O)NR$^{17}$—, the sum of m, n and p is 2.

In another embodiment of the invention as defined anywhere above wherein X is O, and the sum of m, n and p is 1.

In another embodiment of the invention as defined anywhere above, R$^{13}$ is selected from (C$_1$ alkyl)-C(O)NR$^{22}$R$^{23}$; (C$_1$ alkyl)-C(O)OR$^{23}$; and (C$_2$ alkyl)-NR$^{23}$C(O)R$^{22}$.

In a further embodiment of the invention as defined anywhere above, R$^{13}$ is selected from (C$_1$ alkyl)-C(O)NR$^{22}$R$^{23}$ and (C$_1$ alkyl)-C(O)OR$^{23}$.

In a yet further embodiment of the invention as defined anywhere above, R$^{13}$ is (C$_1$ alkyl)-C(O)NR$^{22}$R$^{23}$.

In another embodiment of the invention as defined anywhere above,

R$^{22}$ is selected from H and C$_1$-C$_3$ alkyl;

R$^{23}$ is selected from H; C$_1$-C$_8$ alkyl; C$_3$-C$_8$ cycloalkyl; C$_1$-C$_4$ alkoxy-C$_1$-C$_4$ alkyl; (C$_0$-C$_4$ alkyl)-aryl optionally substituted by one or more groups selected from C$_1$-C$_6$ alkyl, C$_1$-C$_6$ alkoxy and halogen; (C$_0$-C$_4$ alkyl)-3- to 14-membered heterocyclic group, the heterocyclic group including one or more heteroatoms selected from N, O and S, optionally substituted by one or more groups selected from halogen, oxo, C$_1$-C$_6$ alkyl and C(O)C$_1$-C$_8$ alkyl; (C$_0$-C$_4$ alkyl)-O-aryl optionally substituted by one or more groups selected from C$_1$-C$_6$ alkyl, C$_1$-C$_6$ alkoxy and halogen; and (C$_0$-C$_4$ alkyl)-O-3- to 14-membered heterocyclic group, the heterocyclic group including one or more heteroatoms selected from N, O and S, optionally substituted by one or more groups selected from halogen, C$_1$-C$_6$ alkyl and C(O)C$_1$-C$_6$ alkyl; wherein the alkyl groups are optionally substituted by one or more halogen atoms, hydroxyl, C$_1$-C$_4$ alkoxy, C(O)NH$_2$, C(O)NHC$_1$-C$_6$ alkyl or C(O)N(C$_1$-C$_8$ alkyl)$_2$; or R$^{22}$ and R$^{23}$ together with the atom(s) to which they are attached form a 5- to 7-membered heterocycloalkyl group, the heterocycloalkyl group including one or more further heteroatoms selected from N, O and S, the heterocycloalkyl group being optionally substituted by one or more Z groups.

In another embodiment of the invention as defined anywhere above wherein $R^{13}$ is $(C_1-C_3$ alkyl$)$-$NR^{23c}(O)R^{22}$, $R^{22}$ and $R^{23}$ together with the atoms to which they are attached form an oxo substituted 5- to 7-membered heterocycloalkyl group, the heterocycloalkyl group including one or more further heteroatoms selected from N, O and S, the heterocycloalkyl group being optionally further substituted by one or more Z groups. In a further embodiment, $R^{13}$ is $(C_1-C_3$ alkyl$)$-$NR^{23}C(O)R^{22}$, wherein —$NR^{23}C(O)R^{22}$ is represented by formula 3

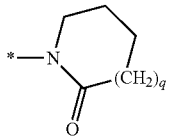

wherein q is 0, 1 or 2, and the asterisk indicates the point of attachment to the $(C_1-C_3$ alkyl)-moiety.

In another embodiment of the invention as defined anywhere above wherein $R^{13}$ is selected from $(C_1-C_3$ alkyl$)$-$C(O)NR^{22}R^{23}$ and $(C_1-C_3$ alkyl$)$-$C(O)OR^{23}$;
$R^{22}$ is selected from H and $C_1-C_3$ alkyl;
$R^{23}$ is selected from H; $C_1-C_8$ alkyl; $C_3-C_8$ cycloalkyl; $C_1-C_4$ alkoxy-$C_1-C_4$ alkyl; $(C_0-C_4$ alkyl)-aryl optionally substituted by one or more groups selected from $C_1-C_6$ alkyl, $C_1-C_6$ alkoxy and halogen; $(C_0-C_4$ alkyl)-3- to 14-membered heterocyclic group, the heterocyclic group including one or more heteroatoms selected from N, O and S, optionally substituted by one or more groups selected from halogen, oxo, $C_1-C_6$ alkyl and $C(O)C_1-C_6$ alkyl; $(C_0-C_4$ alkyl)-O-aryl optionally substituted by one or more groups selected from $C_1-C_6$ alkyl, $C_1-C_6$ alkoxy and halogen; and $(C_0-C_4$ alkyl)-O-3- to 14-membered heterocyclic group, the heterocyclic group including one or more heteroatoms selected from N, O and S, optionally substituted by one or more groups selected from halogen, $C_1-C_6$ alkyl and $C(O)C_1-C_6$ alkyl; wherein the alkyl groups are optionally substituted by one or more halogen atoms, hydroxyl $C_1-C_4$ alkoxy, $C(O)NH_2$, $C(O)NHC_1-C_6$ alkyl or $C(O)N(C_1-C_6$ alkyl$)_2$; or
$R^{22}$ and $R^{23}$ together with the nitrogen to which they are attached form a 5- to 7-membered heterocycloalkyl group, the heterocycloalkyl group including one or more further heteroatoms selected from N, O and S, the heterocycloalkyl group being optionally substituted by one or more Z groups.

In another embodiment of the invention as defined anywhere above, Z is hydroxyl, cyano, nitro, $C_1-C_4$-alkyl, $C_1-C_4$-alkoxy, halogen, $C_1-C_4$-alkylcarbonyl, carboxy, $C_1-C_4$-alkoxycarbonyl, amino, $C_1-C_4$-alkylamino, di-$C_1-C_4$-alkylamino, $C_1-C_4$-alkylaminocarbonyl, di-$C_1-C_4$-alkylaminocarbonyl, $C_1-C_4$-alkylcarbonylamino, $C_1-C_4$-alkylcarbonyl($C_1-C_4$-alkyl)amino, wherein the alkyl and alkoxy groups are each optionally substituted by one or more substituents selected from hydroxyl, halogen, $C_1-C_4$-haloalkyl and $C_1-C_4$-alkoxy groups.

In a yet further embodiment, the invention provides a compound of Formula Ia

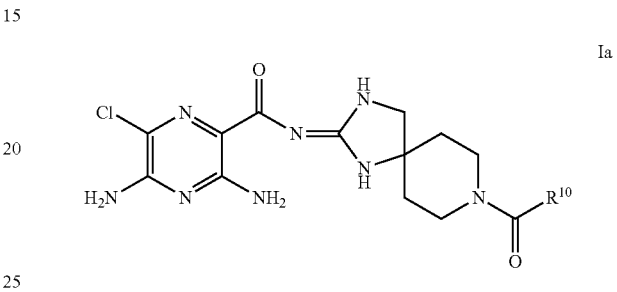

or a pharmaceutically acceptable salt or solvate thereof wherein $R^{10}$ is as defined anywhere above in respect of a compound of Formula I.

In a yet further embodiment, the invention provides a compound of Formula Ib

Ib

Cl, N, O, H, N, H₂N, N, NH₂, N, H, N, B, S, O, R^{11a}, R^{12a}, O, N, H, R^{12b}, OR^{13}, R^{11b} or a pharmaceutically acceptable salt or solvate thereof wherein B, $R^{11a}$, $R^{12a}$, $R^{11b}$, $R^{12b}$ and $R^{13}$ are as defined anywhere above in respect of a compound of Formula I.

In a yet further embodiment, the invention provides a compound of Formula Ic

Ic

Cl, N, O, H, N, H₂N, N, NH₂, N, H, N, B, N, N, R^{11a}, R^{12a}, O, OR^{13}, R^{12b}, R^{11b}, O, R^{15}, R^{17} or a pharmaceutically acceptable salt or solvate thereof wherein B, $R^{11a}$, $R^{12a}$, $R^{11b}$, $R^{12b}$, $R^{13}$ and $R^{15}$ and $R^{17}$ are as defined anywhere above in respect of a compound of Formula In a yet further embodiment, the invention provides a compound of Formula Id

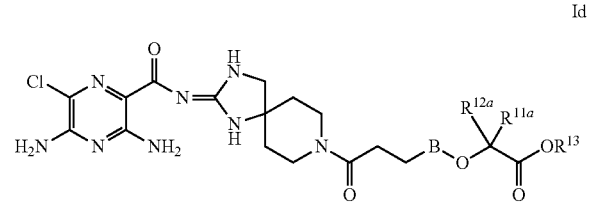

Id or a pharmaceutically acceptable salt or solvate thereof wherein B, $R^{11a}$, $R^{12a}$, and $R^{13}$ are as defined anywhere above in respect of a compound of Formula I.

In another embodiment, individual compounds according to the invention are those listed in the Examples section below.

In another embodiment of the invention, there is provided a compound of Formula I which is selected from:

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester;

[4-(3-{2-[(Z)-3,5-Diamino-6-chloro-pyrazine-2-carbonylimino]-1,3,8-triaza-spiro[4.5]dec-8-yl}-3-oxo-propyl)-phenoxy]-acetic acid [(2-hydroxy-ethyl)-methyl-carbamoyl]-methyl ester;

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid cyclohexyl oxycarbonylmethyl ester;

3-(3-{2-[(E)-3,5-Diamino-6-chloro-pyrazine-2-carbonylimino]-1,3,8-triaza-spiro[4.5]decane-8-carbonyl}-benzene sulfonylamino)-propionic acid cyclohexyloxy carbonylmethyl ester;

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dimethylcarbamoylmethyl ester;

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester;

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid tert-butoxycarbonylmethyl ester;

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid benzyloxycarbonylmethyl ester;

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid diethylcarbamoylmethyl ester;

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid 2-oxo-2-piperidin-1-yl-ethyl ester;

[2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester;

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid 2-oxo-2-(2-trifluoromethyl-pyrrolidin-1-yl)-ethyl ester;

[2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid 2-(2-oxo-piperidin-1-yl)-ethyl ester;

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid 2-morpholin-4-yl-2-oxo-ethyl ester;

1-[(3-{2-[(E)-3,5-Diamino-6-chloro-pyrazine-2-carbonylimino]-1,3,8-triaza-spiro[4.5]decane-8-carbonyl}-benzenesulfonylamino)-methyl]-cyclobutanecarboxylic acid dipropylcarbamoylmethyl ester;

3-[3-(3-{2-[(E)-3,5-Diamino-6-chloro-pyrazine-2-carbonylimino]-1,3,8-triaza-spiro[4.5]decane-8-carbonyl}-phenyl)-ureido]-propionic acid dipropylcarbamoylmethyl ester; and 1-[(3-{2-[(E)-3,5-Diamino-6-chloro-pyrazine-2-carbonylimino]-1,3,8-triaza-spiro[4.5]decane-8-carbonyl}-benzenesulfonylamino)-methyl]-cyclobutanecarboxylic acid 2-oxo-2-(2-trifluoromethyl-pyrrolidin-1-yl)-ethyl ester;

or a pharmaceutically acceptable salt or solvate thereof.

In the embodiments mentioned herein, where only certain variables are defined, it is intended that the remainder of the variables are as defined in any embodiment herein. Thus, the invention provides for the combination of limited or optional definitions of variables.

The following terms as used herein are intended to have the following meanings:

"Optionally substituted" as used herein means the group referred to can be unsubstituted, or substituted at one or two or three positions by any one or any combination of the radicals listed thereafter.

"Halo" or "halogen" as used herein means fluorine, chlorine, bromine or iodine.

"$C_1$-$C_3$ alkyl", "$C_1$-$C_6$ alkyl", "$C_1$-$C_8$ alkyl" and the like, as used herein, denotes a straight chain or branched alkyl group that contains one to three, six or eight (or the relevant number) carbon atoms and which may be substituted as defined.

"Aryl", as used herein, represents an aromatic carbocyclic ring system having 6 to 15 carbon atoms. It can be monocyclic, bicyclic or tricyclic, and may be optionally substituted as defined. Examples of $C_6$-$C_{15}$-aryl groups include but are not limited to phenyl, phenylene, benzenetriyl, indanyl, naphthyl, naphthylene, naphthalenetriyl and anthracenyl.

"Heterocyclyl" or "heterocyclic" refers to a 4- to 14-membered heterocyclic ring system containing at least one ring heteroatom selected from the group consisting of nitrogen, oxygen and sulphur, which may be saturated, partially saturated or aromatic (i.e. heteroaryl). Examples of 4- to 14-membered heterocyclic groups include but are not limited to furan, azetidine, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, pyridinone, morpholine, triazine, oxazine, tetrahydrofuran, tetrahydrothiophene, tetrahydrothiopyran, tetrahydropyran, 1,4-dioxane, 1,4-oxathiane, indazole, quinoline, quinazoline, quinoxaline, indole, indoline, thiazole, thiophene, isoquinoline, isoindole, isoindoline, benzothiophene, benzoxazole, benzisoxazole, benzothiazole, benzisothiazole, benzofuran, dihydrobenzofuran, dihydroisobenzofuran, benzodioxole, benzimidazole, benzotriazole, pyrazolopyridine, pyrazolopyrimidine, imidazopyridine, purine, naphthyridine or tetrahydronaphthyridine. "Heterocyclyl" or "heterocyclic" also includes bridged heterocyclic groups such as 3-hydroxy-8-aza-bicyclo[3.2.1]oct- 8-yl and fused ring systems such as pyridopyrimidine. The 4- to 14-membered heterocyclic group can be unsubstituted or substituted.

"Heterocyclyl" includes heteroaryl and heterocycloalkyl groups.

"Heteroaryl" is an aromatic ring system containing from 5 to 15 ring atoms one or more of which are heteroatoms selected from O, N or S. Preferably there are one or two heteroatoms. Heteroaryl (heterocyclic aryl) represents, for example: pyridyl, indolyl, isoindolyl, indazolyl, quinoxalinyl, quinazolinyl, quinolinyl, isoquinolinyl, naphthryridinyl, pyridopyrimidinyl, benzothienyl, benzofuranyl, benzopyranyl, benzothiopyranyl, benzotriazolyl, pyrazolopyridinyl, furanyl, pyrrolyl, thiazolyl, oxazolyl, isoxazolyl, triazolyl, tetrazolyl, pyrazolyl, imidazolyl, thienyl. The heteroaryl group can be substituted or unsubstituted.

"$C_3$-$C_{10}$-cycloalkyl" denotes a fully saturated carbocyclic ring having 3 to 10 ring carbon atoms, for example a monocyclic group such as a cyclopropyl, cyclobutyl, cyclopentyl or cyclohexyl, cycloheptyl, cyclooctyl, cyclononyl or cyclodecyl, or a bicyclic group such as bicycloheptyl or bicyclooctyl. Different numbers of carbon atoms may be specified, with the definition being amended accordingly. The cycloalkyl group can be substituted or unsubstituted.

"$C_5$-$C_{10}$-cycloalkenyl" denotes a partially saturated carbocyclic ring having 5 to 10 ring carbon atoms, for example a monocyclic group such as a cyclopentenyl or cyclohexenyl, cycloheptenyl, cyclooctenyl or cyclononenyl, or a bicyclic group such as bicycloheptenyl or bicyclooctenyl. The ring or ring system may contain more than one carbon-carbon double bond. Different numbers of carbon atoms may be specified, with the definition being amended accordingly. The cycloalkenyl group can be substituted or unsubstituted.

"$C_1$-$C_8$-haloalkyl" as used herein denotes $C_1$-$C_8$-alkyl as hereinbefore defined substituted by one or more halogen atoms, preferably one, two or three halogen atoms. Different numbers of carbon atoms may be specified, with the definition being amended accordingly.

"$C_1$-$C_8$-alkylamino" as used herein denote amino substituted by one or two $C_1$-$C_8$-alkyl groups as hereinbefore defined, which may be the same or different. Different numbers of carbon atoms may be specified, with the definition being amended accordingly.

"$C_1$-$C_8$-alkoxy" as used herein denotes straight chain or branched alkoxy that contains 1 to 8 carbon atoms. Different numbers of carbon atoms may be specified, with the definition being amended accordingly.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2011).

Furthermore, the compounds of the present invention, including their salts, can also be obtained in the form of their hydrates, or include other solvents used for their crystallization.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included. Tautomers are one of two or more structural isomers that exist in equilibrium and are readily converted from one isomeric form to another. More specifically, for example, compounds of Formula Ia may exist in one or both of the following tautomeric forms:

metric atom has at least 50% enantiomeric excess, at least 60% enantiomeric excess, at least 70%) enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Since the compounds of the invention are intended for use in pharmaceutical compositions it will readily be understood that they are each preferably provided in substantially pure form, for example at least 60% pure, more suitably at least 75% pure and preferably at least 85%, especially at least 98%

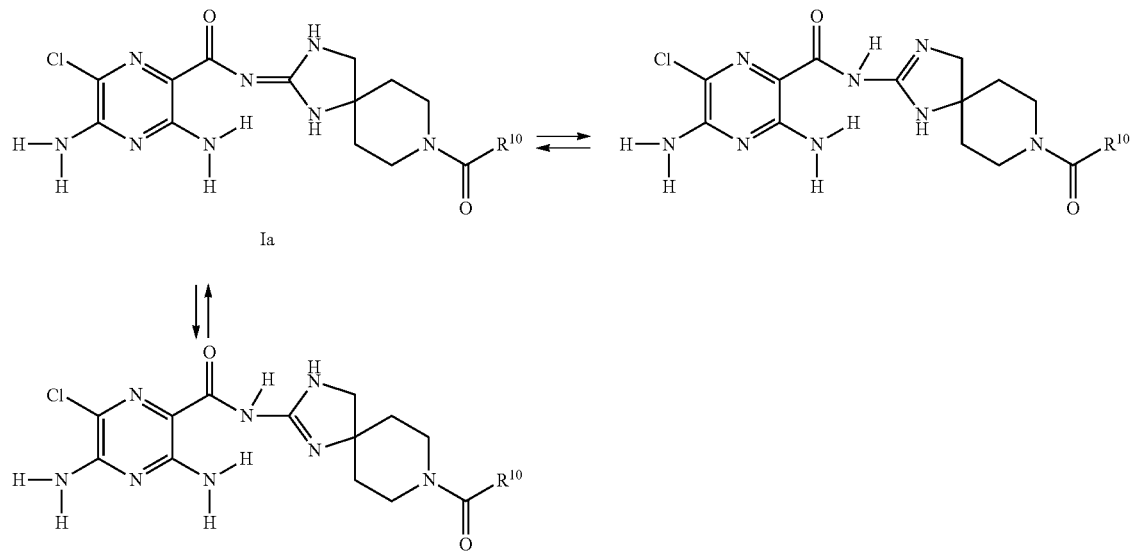

Examples of tautomers include but are not limited to those compounds defined in the claims.

Any asymmetric atom (e.g., carbon or the like) of the compound(s) of the present invention can be present in racemic or enantiomerically enriched, for example the (R)-, (S)- or (R,S)-configuration. In certain embodiments, each asympure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed. Pharmaceutically acceptable solvates in accordance with the invention include those wherein the solvent of crystallization may be isotopically substituted, e.g. $D_2O$, $d_6$-acetone, $d_6$-DMSO.

Synthesis

The compounds of the invention may be synthesized by the general synthetic routes below, specific examples of which are described in more detail in the Examples.

Compounds of formula I may be prepared according to Scheme 1.

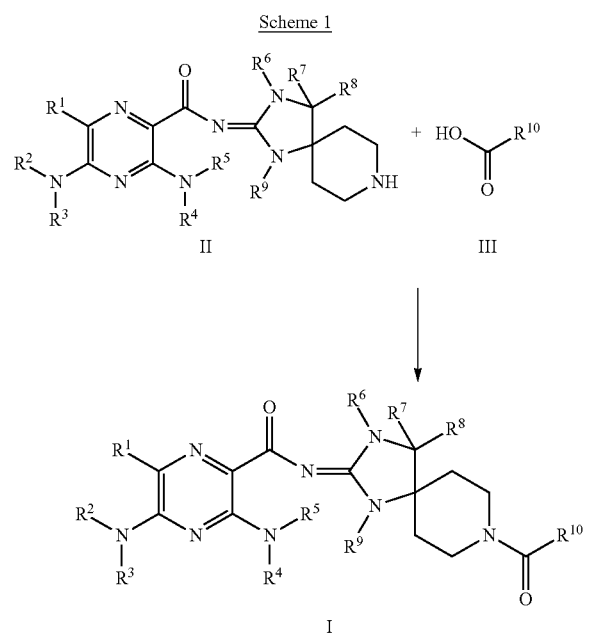

Alternatively, compounds of formula I may be prepared according to Scheme 2.

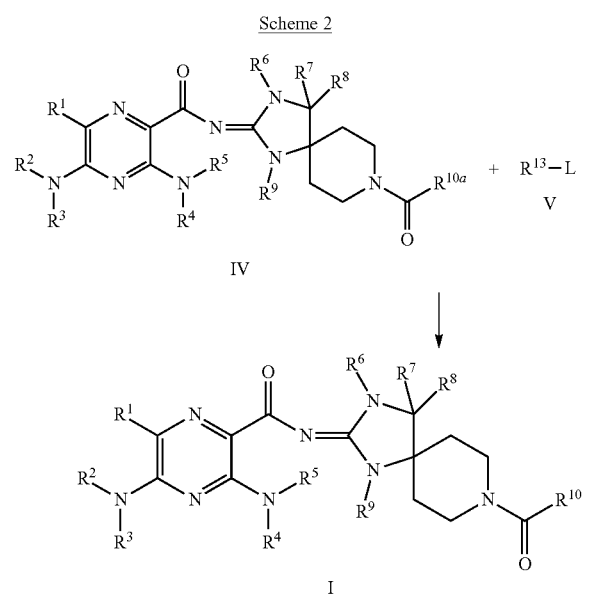

wherein $R^{10a}$ is —($C_0$-$C_3$alkylene)-B—X—$(CR^{11a}R^{12a})_m$—$(CR^{11b}R^{12b})_n$—$(CR^{11c}R^{12c})_p$—C(O)OH, and L is a suitable leaving group.

The above general schemes may be used to prepare compounds of Formula I. The desired specific compounds can be prepared by selecting the appropriate starting materials, reactants and reaction conditions.

The starting materials and reagents in the above scheme are all either available commercially or can be prepared following literature precedents. In particular compounds of Formula II and compounds of Formula IV may be prepared as described in international patent application published as WO2009074575, which document is incorporated herein by reference.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/1, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage). Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers. Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., to room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ. All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

As a further aspect of the present invention, there is also provided a process for the preparation of compounds of formula I or a pharmaceutically acceptable salt or solvate thereof.

According to a further aspect of the invention there is provided a process of preparing a compound of formula I or a pharmaceutically acceptable salt or solvate thereof comprising the step of:

(a) reacting a compound of formula II

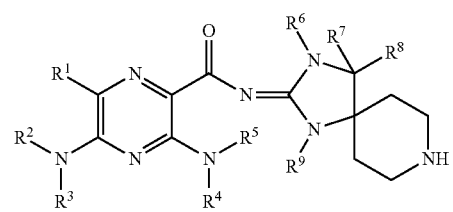

wherein $R^1$, $R^2$, $R^3$, $R^4$, $R^5$, $R^6$, $R^7$, $R^8$ and $R^9$ are as defined anywhere above, with a compound of formula III

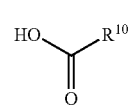

wherein $R^{10}$ are as defined anywhere above, under convention reaction conditions for acid-amine coupling; or (b) reacting a compound of formula IV

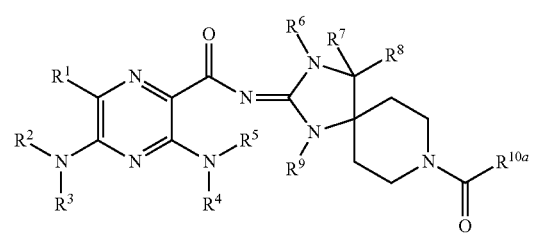

with a compound $R^{13}L$ of formula V under convention reaction conditions
wherein $R^1$, $R^2$, $R^3$, $R^4$, $R^5$, $R^6$, $R^7$, $R^8$, $R^9$ and $R^{13}$ are as defined anywhere above; $R^{10a}$ is —(C$_0$-C$_3$alkylene)-B—X—(CR$^{11a}$R$^{12a}$)$_m$—(CR$^{11b}$R$^{12b}$)$_n$—(CR$^{11c}$R$^{12c}$)$_p$—C(O)OH
wherein B, X, $R^{11a}$, $R^{11b}$, $R^{11c}$, $R^{12a}$, $R^{12b}$, $R^{12c}$, m, n, and p are as defined anywhere above; and L is a leaving group.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

The agents of the invention act to blockade the epithelial sodium channel (ENaC). Having regard to their blockade of the epithelial sodium channel (ENaC), compounds of formula (I), in free or pharmaceutically acceptable salt form, hereinafter alternately referred to as "agents of the invention", are useful in the treatment of conditions which respond to the blockade of the epithelial sodium channel, particularly conditions benefiting from mucosal hydration.

Diseases mediated by blockade of the epithelial sodium channel, include diseases associated with the regulation of fluid volumes across epithelial membranes. For example, the volume of airway surface liquid is a key regulator of mucociliary clearance and the maintenance of lung health. The blockade of the epithelial sodium channel will promote fluid accumulation on the mucosal side of the airway epithelium thereby promoting mucus clearance and preventing the accumulation of mucus and sputum in respiratory tissues (including lung airways). Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Treatment in accordance with the invention may be symptomatic or prophylactic, in particular symptomatic.

Thus in a further aspect the invention includes an agent of the invention for use as a pharmaceutical.

Therefore according to a further aspect, the invention provides an agent of the invention for treating or preventing a disease or condition mediated by blockade of the epithelial sodium channel.

Therefore according to a further aspect, the invention provides the use of an agent of the invention in the manufacture of a medicament for the treatment or prevention of a disease or condition mediated by blockade of the epithelial sodium channel.

Therefore according to a further aspect, the invention provides a method for preventing or treating a disease or condition mediated by blockade of the epithelial sodium channel in which an effective amount of an agent of the invention is administered to a patient in need of such treatment.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

The agents of the invention may also be useful as acid-sensing ion channel (ASIC) blockers. Thus they may be useful in the treatment of conditions which respond to the blockade of the acid-sensing ion channel.

The suitability of epithelial sodium channel blocker as a treatment of a disease benefiting from mucosal hydration, may be tested by determining the inhibitory effect of the channel blocker on ENaC in a suitable cell-based assay. For example single cells or confluent epithelia, endogenously expressing or engineered to overexpress ENaC can be used to assess channel function using electrophysiological techniques or ion flux studies. See methods described in: Hirsh et al., *J Pharm Exp Ther* (2004); Moody et al., *Am J Physiol Cell Physiol* (2005).

In accordance with the foregoing, the invention also provides as a further aspect a method for preventing or treating a condition responsive to blockade of the epithelial sodium channel, e.g., diseases associated with the regulation of fluid volumes across epithelial membranes, particularly an obstructive airways disease, which comprises administering to a subject, particularly a human subject, in need thereof a compound of formula (I), or a pharmaceutically acceptable salt or solvate thereof.

In another aspect the invention provides a compound of formula (I), in free form or a pharmaceutically acceptable salt or solvate thereof, for preventing or treating a condition responsive to blockade of the epithelial sodium channel, particularly an obstructive airways disease, e.g., cystic fibrosis and COPD.

In another aspect the invention provides the use of a compound of formula (I), in free form or a pharmaceutically acceptable salt or solvate thereof, in the manufacture of a medicament for the prevention or treatment of a condition responsive to blockade of the epithelial sodium channel, particularly an obstructive airways disease, e.g., cystic fibrosis and COPD The compounds of the invention have good ENaC blocker activity and may be tested in the following assays.

Cell Culture

Human Bronchial Epithelial cells (HBECs) (Cambrex) were cultured under air-liquid interface conditions to provide a well differentiated mucociliary phenotype.

HBECs were cultured using a modification of the method described by Gray and colleagues (Gray et al., 1996). Cells were seeded in plastic T-162 flasks and were grown in bronchial epithelial cell growth medium (BEGM; Cambrex) supplemented with bovine pituitary extract (52 μg/mL), hydrocortisone (0.5 μg/mL), human recombinant epidermal growth factor (0.5 ng/mL), epinephrine (0.5 μg/mL), transferrin (10 µg/mL), insulin (5 µg/mL), retinoic acid (0.1 µg/mL), triiodothyronine (6.5 µg/mL), gentamycin (50 µg/mL) and amphotericin B (50 ng/mL). Medium was changed every 48 hours until cells were 90% confluent. Cells were then passaged and seeded ($8.25 \times 10^5$ cells/insert) on polycarbonate Snapwell inserts (Costar) in differentiation media containing 50% DMEM in BEGM with the same supplements as above but without triiodothyronine and a final retinoic acid concentration of 50 nM (all-trans retinoic acid). Cells were maintained submerged for the first 7 days in culture, after which time they were exposed to an apical air interface for the remainder of the culture period. At this time, media was changed to DMEM:F12 media containing 2% v/v Ultroser G for the remainder of culture. Amphotericin B was removed from all media 3 feeds prior to use in the Ussing Chambers. Cells were used between days 7 and 21 after establishment of the apical-air interface. At all stages of culture, cells were maintained at 37° C. in 5% $CO_2$ in an air incubator.

Short Circuit Current (ISC) Measurements

Snapwell inserts were mounted in Vertical Diffusion Chambers (Costar) and were bathed with continuously gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$, and 10 glucose. The solution osmolarity was between 280 and 300 mOsmol/kg $H_2O$ for all physiological salt solutions used. Cells were voltage clamped to 0 mV (model EVC4000; WPI). RT was measured by applying a 1- or 2-mV pulse at 30-s intervals and calculating RT by Ohm's law. Data were recorded using a PowerLab workstation (ADInstruments).

Test compounds were prepared as a 10 mM stock solution in DMSO (95%). Serial 3-fold dilutions were freshly prepared in an appropriate vehicle (distilled $H_2O$ or Ringers solution). The initial concentration was added to the apical chamber as a 1000× concentrate in 5 µL, resulting in a final 1× concentration the 5 mL volume of the Ussing chamber. Subsequent additions of compound were added in a 3.3 µL volume of the 1000× serially diluted stock solution. At the completion of the concentration-response experiment, amiloride (10 µM) was added into the apical chamber to enable the total amiloride-sensitive current to be measured. An amiloride control $IC_{50}$ was established at the start of each experiment.

Results are expressed as the mean % inhibition of the amiloride-sensitive ISC. Concentration-response curves were plotted and $IC_{50}$ values generated using GraphPad Prism 3.02 or Graphpad Prism 4. Cell inserts were typically run in duplicate and the $IC_{50}$ calculated on the mean % inhibition data.

The compounds of the Examples herein below generally have $IC_{50}$ values below 10 µM, typically below 1 µM. For instance, the following Examples have the stated $IC_{50}$ values.

| Example | HBEC-ENaC/IC50 [umol l−1] |
| --- | --- |
| 1.0 | 0.017 |
| 1.1 | 0.419 |
| 1.2 | 0.010 |
| 1.3 | 0.003 |
| 1.4 | 0.302 |
| 2.0 | 0.032 |
| 2.1 | 0.030 |
| 2.2 | 0.012 |
| 2.3 | 0.089 |
| 2.4 | 0.110 |
| 3.0 | 0.011 |
| 4.0 | 0.101 |
| 4.1 | 0.132 |
| 4.2 | 0.45 |
| 5.0 | 0.012 |
| 5.1 | 0.031 |
| 5.2 | 0.019 |

The agents of the invention may be administered by any appropriate route, e.g. orally, for example in the form of a tablet or capsule; parenterally, for example intravenously; topically to the skin; intranasally, for example in the treatment of allergic rhinitis; or, preferably, by inhalation, particularly in the treatment of obstructive or inflammatory airways diseases. In particular, the agents of the invention may be delivered as an inhalable formulation for the treatment of COPD, cystic fibrosis or asthma.

In another aspect, the present invention provides a pharmaceutical composition comprising a compound of the present invention and a pharmaceutically acceptable carrier.

The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, ag., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042 (including the BREEZHALER™ device), WO 97/20589 (including the CERTIHALER™ device), WO 97/30743 (including the TWISTHALER™ device), WO 05/37353 (including the GYROHALER™ device), U.S. Pat. No. 6,536,427 (including the DISKUS™ device), WO 97/25086 (including the DISKHALER™ device), WO 95/14089 (including the GEMINI™ device), WO 03/77979 (including the PROHALER™ device), and also the devices disclosed in WO 08/51621, WO 09/117,112 and US 2005/0183724.

The invention also includes (A) an agent of the invention in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by blockade of the epithelial sodium channel. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

The compounds of, formula (I) and their pharmaceutically acceptable salts and solvates have the advantage that they are more selective, have a more rapid onset of action, are more potent, are better absorbed, are more stable, are more resistant to metabolism, have a reduced 'food effect', have an improved safety profile or have other more desirable properties (e.g. with respect to solubility or hygroscopicity) than the compounds of the prior art.

In particular, the compounds of the invention exhibit an advantageous stability profile in human plasma. In providing compounds which exhibit an advantageous stability profile in human plasma, the invention provides compounds which effectively blockade the epithelial sodium channel (ENaC) with improved pharmacokinetics.

The stability of the compounds of the invention in human plasma may be measured as follows:
Stability in Human Plasma Blood was taken from healthy volunteers in lithium heparin tubes and plasma was prepared by centrifugal separation of blood cells at 1500 g. Plasma from at least 3 individuals was pooled and used for compound stability determination.

Compounds were prepared in 100% DMSO at a concentration of 10 mM and serially diluted to a concentration of 100 µM. Incubations were performed at a final concentration of 1 µM and were initiated by addition of 3 µl of 100 µM compound stock solution into 297 µl plasma, pre-warmed in a water bath to 37° C., followed by brief vortex mixing. 50 µl aliquots of plasma were removed at 4 timepoints over a 1 hour incubation period and quenched immediately by protein precipitation achieved by addition of the aliquot of plasma to a pre-prepared 96 well plate containing 150 µl of acetonitrile containing an appropriate internal standard. Acetonitrile quenched samples were vortex mixed followed by centrifugation for 20 minutes at 1500 g to remove the precipitated proteins. Initial compound levels (at time=0 minutes) was established by spiking compound into pre-quenched plasma at the same concentration as used in the incubation. The supernatant was then removed, diluted 1:1 with water and analysed for compound remaining by liquid chromatography-tandem mass spectrometry (Waters Acquity HPLC, Applied Biosystems API4000). The plasma elimination rate constant of the compound was calculated by fitting the peak area ratio of compound:internal standard to an exponential decay function and the half life calculated by division of the natural log of 2 by the elimination rate constant (Microsoft Excel).

The following Examples have the stated half life in human plasma values.

| Example | Half life in human plasma (mins) |
| --- | --- |
| 1.0 | 2 |
| 1.2 | 3 |
| 1.3 | 4 |
| 2.0 | 1 |
| 2.1 | 5 |
| 3.0 | 2 |
| 4.0 | 28 |
| 4.1 | 3 |
| 4.2 | 4 |
| 5.0 | 5 |
| 5.1 | 2 |
| 5.2 | 39 |

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by blockade of the epithelial sodium channel, wherein the medicament is prepared for administration with another therapeutic agent. The invention also provides the use of another therapeutic agent for treating a disease or condition mediated by blockade of the epithelial sodium channel, wherein the medicament is administered with a compound of formula (I).

The invention also provides a compound of formula (I) for use in a method of treating a disease or condition mediated by blockade of the epithelial sodium channel, wherein the compound of formula (I) is prepared for administration with another therapeutic agent. The invention also provides another therapeutic agent for use in a method of treating a disease or condition mediated by blockade of the epithelial sodium channel, wherein the other therapeutic agent is prepared for administration with a compound of formula (I). The invention also provides a compound of formula (I) for use in a method of treating a disease or condition mediated by blockade of the epithelial sodium channel, wherein the compound of formula (I) is administered with another therapeutic agent. The invention also provides another therapeutic agent for use in a method of treating a disease or condition mediated by blockade of the epithelial sodium channel, wherein the other therapeutic agent is administered with a compound of formula (I).

The invention also provides the use of a compound of formula (I) for treating a disease or condition mediated by blockade of the epithelial sodium channel, wherein the patient has previously (e.g. within 24 hours) been treated with another therapeutic agent. The invention also provides the use of another therapeutic agent for treating a disease or condition mediated by blockade of the epithelial sodium channel, wherein the patient has previously (e.g. within 24 hours) been treated with a compound of formula (I).

In one embodiment, the other therapeutic agent is selected from anti-inflammatory, bronchodilatory, antihistamine, decongestant and anti-tussive drug substances, particularly in the treatment of cystic fibrosis or obstructive or inflammatory airways diseases such as those mentioned hereinbefore, e.g., as potentiators of therapeutic activity of such drugs or as a means of reducing required dosaging or potential side effects of such drugs.

Accordingly, the invention includes as a further aspect a combination of an epithelial sodium channel blocker of the present invention with osmotic agents (hypertonic saline, dextran, mannitol, Xylitol), modifiers of CFTR function, both wild-type and mutant (correctors and potentiators), e.g., those described in WO 2007/021982, WO 2006/099256, WO 2006/127588, WO 2004/080972, WO 2005/026137, WO 2005/035514, WO 2005/075435, WO 2004/111014, WO 2006/101740, WO 2004/110352, WO 2005/120497 and US 2005/0176761, an anti-inflammatory, bronchodilatory, antihistamine, anti-tussive, antibiotic or DNase drug substance, said epithelial sodium channel blocker and said drug substance being in the same or different pharmaceutical composition.

Suitable modifiers of CFTR function include CFTR potentiators, in particular the compound VX-770 of formula

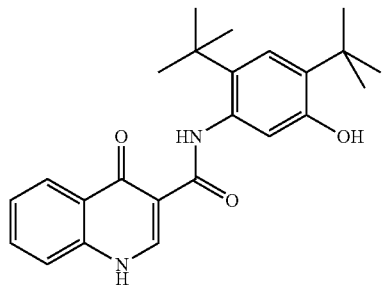 [SMILES: CC(C)(C)c1cc(C(C)(C)C)c(NC(=O)c2c[nH]c3ccccc3c2=O)cc1O]

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of epithelial sodium channel blockers with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden),V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula:

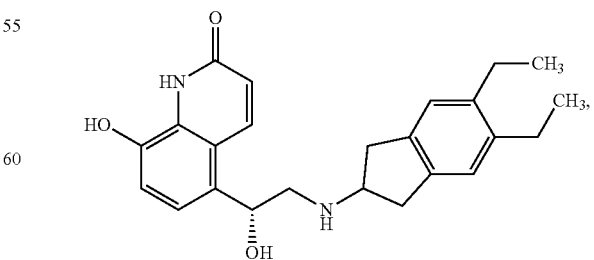

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by the epithelial sodium channel, or (ii) associated with epithelial sodium channel activity, or (iii) characterized by activity (normal or abnormal) of the epithelial sodium channel; or (2) reducing or inhibiting the activity of the epithelial sodium channel. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of the epithelial sodium channel.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The invention is illustrated by the following Examples.

EXAMPLES

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

General Conditions:

Mass spectra were run on LCMS systems using electrospray ionization. These were either Agilent 1100 HPLC/Micromass Platform Mass Spectrometer combinations, or Agilent 1200 HPLC/Agilent 6130 Quadropole Mass Spectrometer combinations, or Waters Acquity HPLC with SQD Mass Spectrometer. [M+H]$^+$ refers to mono-isotopic molecular weights.

NMR spectra were run on open access Bruker AVANCE 400 NMR spectrometers using ICON-NMR. Spectra were measured at 298K and were referenced using the solvent peak. Some protons were not observed directly due to the very broad nature of their exchangeable resonances.

The following examples are intended to illustrate the invention and are not to be construed as being limitations thereon. Temperatures are given in degrees centigrade. If not mentioned otherwise, all evaporations are performed under reduced pressure. The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

Abbreviations:

| | |
|---|---|
| Br | broad |
| d | doublet |
| DCM | dichloromethane |
| DSC | differential scanning calorimetry |
| DMF | N,N-dimethylformamide |
| DMI | 1,3-dimethyl-2-imidazolidinone |
| DMSO | dimethylsulfoxide |
| EDCI | N-(3-dimethylaminopropyl)-N'-ethylcarbodiimide |
| EtOAc | EtOAc |
| h | hour(s) |
| HOBt | 1-hydroxybenzotriazole |
| HPLC | high pressure liquid chromatography |
| LC-MS | liquid chromatography and mass spectrometry |
| MeOH | methanol |
| MS | mass spectrometry |
| m | multiplet |
| 2-meTHF | 2-methyltetrahydrofuran |
| min | minutes |
| ml | milliliter(s) |
| m/z | mass to charge ratio |
| NMR | nuclear magnetic resonance |
| iPrOH | isopropanol |
| ppm | parts per million |
| PS | polymer supported |
| PEAX | PE-anion exchange (e.g. Isolute ® PE-AX columns from Biotage) |
| Rt | retention time |
| s | singlet |
| SCX-2 | strong cation exchange (e.g. Isolute ® SCX-2 columns from Biotage) |
| t | triplet |
| TEA | triethylamine |
| TFA | trifluoroacetic acid |
| THF | tetrahydrofuran |

Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:

| Method 2 minLC_v002 | |
|---|---|
| Column | Waters BEH C18 50 × 2.1 mm, 1.7 μm |
| Column Temperature | 50° C. |
| Eluents | A: $H_2O$, B: methanol, both containing 0.1% TFA |
| Flow Rate | 0.8 ml/min |
| Gradient | 0.20 min 5% B; 5% to 95% B in 1.30 min, 0.25 min 95% B |

| Method 2 minLC_v003 | |
|---|---|
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 mL/min |
| Gradient | 0.20 min 5% B; 5% to 95% B in 1.30 min, 0.25 min 95% B |

| Method 10 minLC_v002 | |
|---|---|
| Column | Waters BEH C18 50 × 2.1 mm, 1.7 μm |
| Column Temperature | 50° C. |
| Eluents | A: $H_2O$, B: methanol, both containing 0.1% TFA |
| Flow Rate | 0.8 mL/min |
| Gradient | 0.20 min 5% B; 5% to 95% B in 7.80 min, 1.00 min 95% B |

| Method 10 minLC_v003 | |
|---|---|
| Column | Waters BEH C18 50 × 2.1 mm, 1.7 μm |
| Column Temperature | 50° C. |
| Eluents | A: $H_2O$, B: acetonitrile, both containing 0.1% TFA |
| Flow Rate | 0.8 mL/min |
| Gradient | 0.20 min 5% B; 5% to 95% B in 7.80 min, 1.00 min 95% B |

| Method (i) | |
|---|---|
| Column | Agilent Zorbax SB-C18 (Rapid resolution) 30 × 2.1 mm, 3.5 μm |
| Column Temperature | 30° C. |
| Eluents | B: $H_2O$, C: acetonitrile, both containing 0.1% formic acid |
| Flow Rate | 0.8 mL/min |
| Gradient | 1 min 5% C; 5% to 95% C in 5 min, 3.00 min 95% C |

-continued

| Method (ii) | |
|---|---|
| Column | SB-C18 50 × 4.6 mm, 1.8 μM |
| Column Temperature | 30° C. |
| Eluents | A: H$_2$O, B: acetonitrile, both containing 0.1% formic acid |
| Flow Rate | 1 mL/min |
| Gradient | 1 min 2% B; 2% to 70% B in 4 min, 70% to 90% B in 0.1 min, 4.9 min 95% B |

Example compounds of the present invention include:

Preparation of Final Compounds

Example 1.0

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt

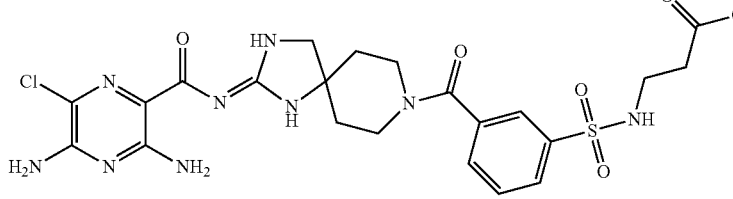

Step 1: 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester The title compound may be prepared by either Method A or B Method A:

To a stirred solution of 3-(2-dipropylcarbamoylmethoxycarbonyl-ethylsulfamoyl)-benzoic acid (Int. AA) (7.0 g, 16.89 mmol) in DMF at RT was added 3,5-diamino-6-chloro-pyrazine-2-carboxylic acid [1,3,8-triaza-spiro[4.5]dec-(2E)-ylidene]-amide hydrochloride (WO09074575, Ex. 38, page 123) (8.20 g, 16.89 mmol) followed by N-methylmorpholine (7.43 ml, 67.6 mmol). The reaction mixture was stirred at RT for 10 min and treated with HATU (6.42 g, 16.89 mmol) in one portion. The mixture was stirred at RT for a further 10 min and then the reaction was quenched by addition of ice-water (500 ml). The resulting solid was collected by filtration and dissolved in DCM. The solution was washed with water (1×500 ml), dried (MgSO$_4$) and concentrated in vacuo to give a crude orange oil. Purification by chromatography on silica eluting with DCM/iPA (2% TEA) afforded the title compound as the hexafluorophosphate salt; LC-MS Rt 3.72 mins; 721.5 [M+H]$^+$, Method 10minLC_v003.; $^1$H NMR (400 MHz, DMSO-d6) δ 8.52 (1H, br s), 8.35 (1H, br s), 7.88 (2H, dt), 7.77 (1H, s), 7.72-7.65 (2H, m), 6.72 (2H, br s), 4.73 (2H, s), 3.80 (1H, b s), 3.61 (1H, b s), 3.43 (3H, b s), 3.17-3.09 (4H, m), 3.04 (2H, t), 2.53 (2H, under DMSO), 1.78 (2H, b s), 1.69 (2H, b s), 1.56-1.38 (4H, m), 0.84 (3H, t), 0.78 (3H, t)

Method B:

To a stirred solution of 3-(2-dipropylcarbamoylmethoxycarbonyl-ethylsulfamoyl)-benzoic acid (Int. AA) (6.1 g, 12.60 mmol) in THF (50 ml) was added sequentially water (25 ml), N-methylmorpholine (7 ml, 63 mmol) and HOBt hydrate (2.9 g, 18.9 mmol). The internal temperature was maintained at ≦20° C. 3,5-Diamino-6-chloro-pyrazine-2-carboxylic acid [1,3,8-triaza-spiro[4.5]dec-(2E)-ylidene]-amide hydrochloride (WO09074575, Ex. 38, page 123) (65% purity, 6.3 g, 12.6 mmol) was added and stirred until a clear solution had formed. EDCI.HCl (3.6 g, 18.9 mmol) was added, and the reaction was stirred at RT for 24 h. 2-MeTHF (200 ml) and 2% aq. Na$_2$CO$_3$ (150 ml) were added to the reaction mixture. The layers were separated, and the aqueous phase washed with additional 2-MeTHF (100 ml). The combined organic layers were washed with 2% aq. Na$_2$CO$_3$ (200 ml) and water (2×200 ml). Acetonitrile (100 ml) was added, and the solution concentrated at 30° C. to a volume of 70 ml. Acetonitrile (300 ml) was added, and the solution concentrated again at 30° C. to a volume of 150 ml. The solution was heated to 50° C. and maleic acid (1.62 g) was added to the resulting solution. An off-white precipitate formed immediately, the temperature was allowed to cool to RT over 1 h. The solid was collected by filtration to afford 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester as a maleate salt; DCM (200 ml) and 2% aq. Na$_2$CO$_3$ (200 ml) were added and stirred until the solid had fully dissolved. The organic layer was separated, washed with water (2×100 ml) and concentrated in vacuo to afford the title compound. LC-MS 722.1 [M+H]$^+$, Method (i).; $^1$H NMR (400 MHz, DMSO-d6) δ 9.12-7.57 (4H, br), 7.88 (1H, m), 7.77 (1H, m), 7.70 (1H, m), 7.68 (1H, m), 7.05-6.50 (2H, br s), 6.95-6.20 (1H, br s), 4.73 (2H, s), 3.81-3.39 (2H, m), 3.61-3.31 (2H, m), 3.43 (2H, br s), 3.15-3.11 (4H, m), 3.04 (2H, t), 2.51 (2H, t), 1.79-1.69 (m, 4H), 1.51-1.43 (4H, m), 0.84 (3H, t), 0.78 (3H, t)

Step 2: 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester succinate salt The title compound may be prepared by either Method C or D
Method C:
Succinic acid (409 mg, 3.47 mmol) was added to a solution of 3-(3-{2-[(E)-3,5-diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (step 1, Method B)(2.50 g, 3.47 mmol) in acetonitrile (25 ml) and water (1.5 ml) at 50° C. The resulting clear solution was cooled to RT over 30 mins. Crystallisation started to occur at an internal temperature of −30° C. The resulting slurry was stirred for at RT for 16 h, The crystals were collected by filtration, and the filter cake washed with acetonitrile/water (95:5) and dried at 50° C. under vacuum to afford the title compound;
Method D:
A mixture comprising succinic acid (0.50 g, 4.23 mmol) and acetone (20 g) was heated to 45° C. until a clear solution formed and then filtered (0.2 μm PTFE filter).

In a second reaction vessel, 3-(3-{2-[(E)-3,5-diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (step 1, Method B) (3.00 g, 4.16 mmol) and acetone (30 g) were heated to 45° C. until a clear solution formed and then filtered (0.2 μm PTFE filter).

The solution of succinic acid (0.50 g, 4.23 mmol) in acetone (20 ml) was heated at 45° C. for 1 h and treated with a portion of the solution of 3-(3-{2-[(E)-3,5-diamino-6-chloro-pyrazine-2-carbonylimino]-1,3,8-triaza-spiro[4.5]decane-8-carbonyl}-benzenesulfonyl amino)-propionic acid dipropylcarbamoylmethyl ester in acetone (1.62 g of solution) over 10 min. The resulting mixture was treated with a suspension of seed crystals of 3-(3-{2-[(E)-3,5-diamino-6-chloro-pyrazine-2-carbonylimino]-1,3,8-triaza-spiro[4.5]decane-8-carbonyl}-benzenesulfonylamino)-propionic acid dipropylcarbamoylmethyl ester (as prepared using method C, 20 mg) in acetone (300 mg) and stirred at 45° C. for 30 min. The remaining solution of 3-(3-{2-[(E)-3,5-diamino-6-chloro-pyrazine-2-carbonylimino]-1,3,8-triaza-spiro[4.5]decane-8-carbonyl}-benzenesulfonylamino)-propionic acid dipropylcarbamoyl methyl ester in acetone (31.38 g) was added to the mixture over 5 h and heating continued at 45° C. for 1 h. The suspension was cooled to 25° C. over 1 h and stirred for a further 1 h. The suspension was filtered over a glass frit and the filter cake was washed with acetone (2×5 g). The filter cake was dried at 50° C. to afford the title compound; HPLC Rt 4.02 min, method ii; $^1$H NMR (400 MHz, DMSO-d6) δ 7.87 (1H, m), 7.78 (1H, m), 7.69 (1H, m), 7.68 (1H, m), 6.85 (2H, br s), 4.73 (2H, s), 3.84-3.20 (6H and water, br hump), 3.17-3.09 (4H, m), 3.04 (2H, t), 2.53 (2H, under DMSO), 2.39 (4H, s), 1.80 (2H, br s), 1.70 (2H, br s), 1.55-1.37 (4H, m), 0.85 (3H, t), 0.78 (3H, t) (Please note: The two exchangeable succinate protons and 3-4 acidic NH resonances were not observed directly due to the very broad nature of some of the exchangeable resonances; Melting Temperature $T_m$ (DSC)=149° C.

The compounds of the following tabulated Examples (Table 1) were prepared by a similar method to that of Example 1.0 replacing 3-(2-dipropylcarbamoylmethoxycarbonyl-ethylsulfamoyl)-benzoic acid (Int. AA) with the appropriate Intermediate (the preparations of which are described hereinafter or are commercially available).

TABLE 1

| Ex. | Name | [M + H]+/NMR |
|---|---|---|
| 1.1 | [4-(3-{2-[(Z)-3,5-Diamino-6-chloro-pyrazine-2-carbonylimino]-1,3,8-triaza-spiro[4.5]dec-8-yl}-3-oxo-propyl)-phenoxy]-acetic acid [(2-hydroxy-ethyl)-methyl-carbamoyl]-methyl ester | $^1$H NMR (400 MHz, DMSO-d6) δ 8.67 (1H, s), 8.44 (1H, m), 7.45 (1H, m), 7.16 (2H, d), 6.88 (2H, d), 5.76 (1H, s), 4.97 (1H, s), 4.89 (1H, m). 4.81 (2H, d), 3.75 (1H, m), 3.68-3.4 (6H, m), 2.96 (1H, s), 2.83 (2H, s), 2.75 (2H, t), 2.61 (2H, t), 1.67 (4H, m). LC-MS Rt 1.04 mins; 646.5[M + H]+, Method 2 minLC_v002. |
| 1.2 | [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid cyclohexyl oxycarbonylmethyl ester | $^1$H NMR (400 MHz, DMSO-d6) δ 8.98-8.27 (2H, b hump), 7.43-6.40 (NH2, b hump), 7.17 (2H, d), 6.86 (2H, d), 4.85 (2H, s), 4.77-4.71 (3H, m), 3.76-3.65 (1H, m), 3.62-3.57 (1H, m), 3.50-3.41 (2H, m), 3.39-3.33 (1H, m), 2.75 (2H, t), 2.59 (2H, t), 1.79-1.74 (2H, m), 1.71-1.59 (6H, m), 1.51-1.19 (7H, m). LC-MS Rt 1.31 mins; 671.3/673.3[M + H]+, Method 2 minLC_v002. |
| 1.3 | 3-(3-{2-[(E)-3,5-Diamino-6-chloro-pyrazine-2-carbonylimino]-1,3,8-triaza-spiro[4.5]decane-8-carbonyl}-benzene sulfonylamino)-propionic acid cyclohexyloxy carbonylmethyl ester | 1H NMR (400 MHz, DMSO-d6) δ 8.52 (NH, b s), 8.35 (NH, b s), 7.88 (2H, dt), 7.77 (1H, s), 7.72-7.66 (2H, m), 6.71 (NH2, b s), 4.73-4.67 (1H, m), 4.59 (2H, s), 3.79 (1H, b s), 3.61 (1H, b s), 3.43 (3H, b s), 3.02 (2H, t), 2.55 (2H, t), 1.82-1.57 (8H, m), 1.47-1.17 (6H, m). LC-MS Rt 3.99 mins; 720.5[M + H]+, Method 10 minLC_v003. |
| 1.4 | [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dimethylcarbamoylmethyl ester | 1H NMR (400 MHz, DMSO-d6) δ 8.45 (2H, b s), 7.16 (2H, d), 6.88 (2H, d), 6.77 (NH2, b s), 4.80 (2H, s), 4.01 (2H, s), 3.71-3.62 (1H, m), 3.61-3.52 (1H, m), 3.45-3.35 (4H, m), 2.917 (3H, s), 2.82 (3H, s), 2.75 (2H, t), 2.59 (2H, t), 1.68-1.54 (4H, m). LC-MS Rt 3.07 mins; 616.4/618.4 [M + H]+, Method 10 minLC_v002. |

TABLE 1-continued
| Ex. | Structure |
|---|---|
| 1.1 | 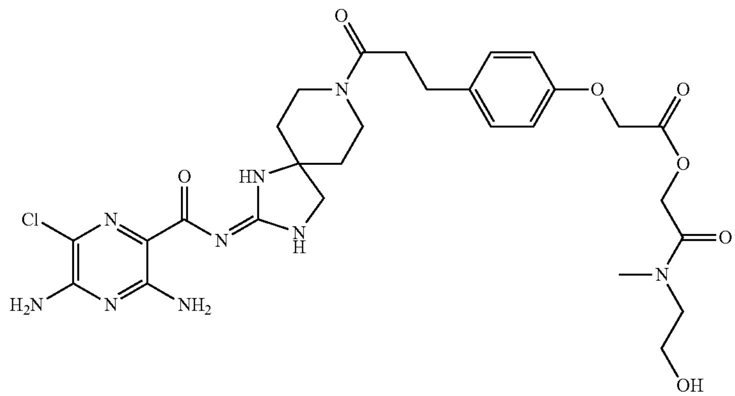 [SMILES: CN(CCO)C(=O)COC(=O)COc1ccc(CCC(=O)N2CCC3(CC2)CN/C(=N/C(=O)c2nc(Cl)c(N)nc2N)N3)cc1] |
| 1.2 | 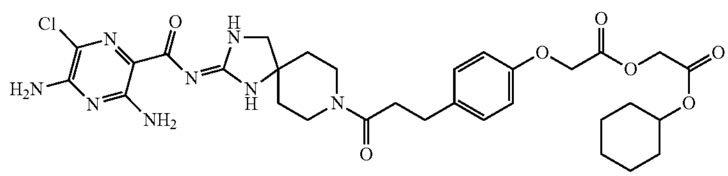 [SMILES: Nc1nc(N)c(C(=O)/N=C2\NCC3(CCN(C(=O)CCc4ccc(OCC(=O)OCC(=O)OC5CCCCC5)cc4)CC3)N2)nc1Cl] |
| 1.3 | 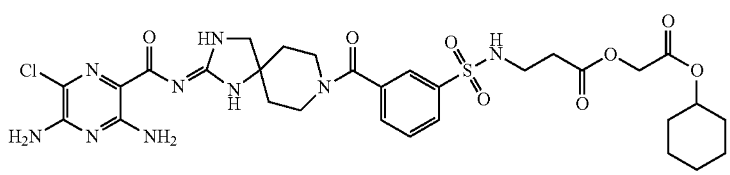 [SMILES: Nc1nc(N)c(C(=O)/N=C2\NCC3(CCN(C(=O)c4cccc(S(=O)(=O)NCCC(=O)OCC(=O)OC5CCCCC5)c4)CC3)N2)nc1Cl] |
| 1.4 | 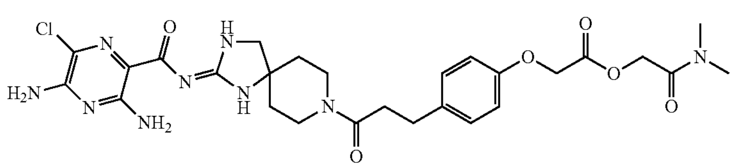 [SMILES: CN(C)C(=O)COC(=O)COc1ccc(CCC(=O)N2CCC3(CC2)CN/C(=N\C(=O)c2nc(Cl)c(N)nc2N)N3)cc1] |
Example 2.0
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester
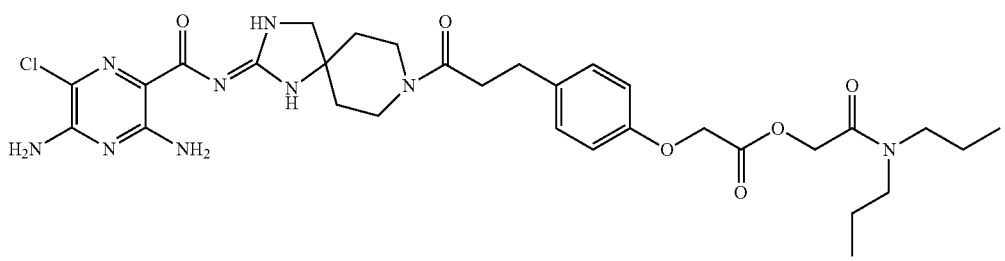 [SMILES: CCCN(CCC)C(=O)COC(=O)COc1ccc(CCC(=O)N2CCC3(CC2)CN/C(=N\C(=O)c2nc(Cl)c(N)nc2N)N3)cc1]

The title compound may be prepared by either Method A or B:

Method A

To a suspension of [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid tert-butyl ester, (WO09074575, Ex. 71, page 134) (6.0 g, 8.2 mmol) in 2-MeTHF/Water (60 ml/10 ml) was added NaOH (1.0 g, 25 mmol) portionwise. The reaction mixture was stirred at RT for 2 h. The organic layer was separated and washed with water (3×10 ml). Water (60 ml) was added and the 2-MeTHF was removed in vacuo THF (30 ml) was added, followed by NaOH (0.68 g, 17 mmol). The reaction mixture was stirred at RT overnight. The organic solvent was removed in vacuo, and the remaining aqueous phase was washed with MTBE (2×30 ml). DMF (30 ml) was added, and the pH adjusted to 7 with 4N HCl (4.25 ml) at RT. PhMe azotropical distillation was performed three times. NaHCO$_3$ (1.0 g, 11.9 mmol) and 2-chloro-N,N-dipropyl-acetamide (2.2 g, 12.4 mmol) were added to the remaining solution, and the resulting reaction mixture was heated at 60° C. overnight. The mixture was partitioned between DCM (60 ml) and water (30 ml). The organic phase was washed with water/sat. aq. NaHCO$_3$ (10:1,

Method B

Step 1: [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid tert-butyl ester (WO09074575, Ex. 71, page 134) (28.4 g, 48.4 mmol) was slurried in 1,4-dioxane (260 ml) and stirred for 1 h. 4N HCl in dioxane (121 ml, 484 mmol) was added dropwise over 15 min and the reaction mixture was stirred overnight. The resulting yellow solid was filtered and washed with diethyl ether. The solid was slurried in fresh diethyl ether (500 ml) and sonicated for 30 min. The resulting solid was collected by filtration and dried in vacuo to afford the title product as a mono hydrochloride, di-dioxan solvate; LC-MS Rt 0.79 rains; 531.3 and 533.3 [M+H]$^+$, Method 2minLC_v003.

Step 2: [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester

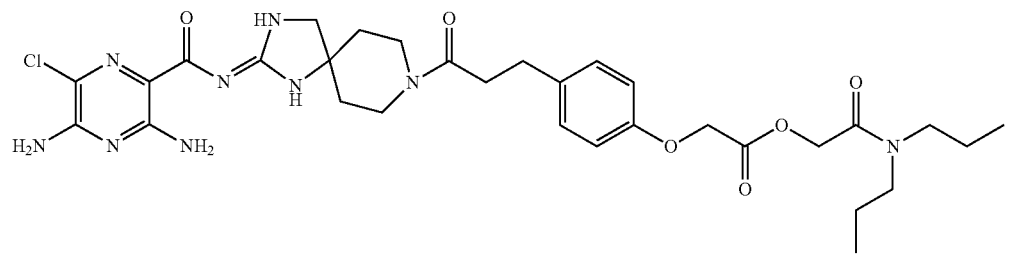 [SMILES: CCCN(CCC)C(=O)COC(=O)COc1ccc(CCC(=O)N2CCC3(CC2)CN/C(=N\C(=O)c2nc(Cl)c(N)nc2N)N3)cc1]

5×30 ml), water (30 ml) and concentrated in vacuo to a volume of ~20 ml. 5 ml of the DCM solution was added to isopropyl acetate (20 ml) while stirring at RT. The DCM was removed in vacuo. This procedure was repeated until all the DCM solution was added. The resulting suspension was filtered to afford crude [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dipropyl carba moylmethyl ester as an off-white solid. The solid was suspended in iPrOH (50 ml) and heated to 60° C. for 3 h. A white suspension formed which was cooled to RT and the solid collected by filtration, and dried under vacuum to afford the title compound; $^1$H NMR (400 MHz, DMSO-d6) δ 8.42 (1, s), 8.36 (1H, s), 7.15 (2H, d), 6.86 (2H, d), 6.72 (2H, br s), 4.88 (2H, s), 4.81 (2H, s), 3.62, 3.40 (2H, m), 3.56, 3.37 (2H, m), 3.38 (2H, s), 3.18-3.12 (4H, m), 2.74 (2H, t), 2.59 (2H, t), 1.67-1.54 (4H, m), 1.54, 1.45 (4H, AB), 0.85 (3H, t), 0.80 (3H, t). LC-MS Rt 5.08 mins; 672.3 [M+H]$^+$, Method (i)

A solution of [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid (Step 1) (811 mg, 1.53 mmol) in DMF (30 ml) was treated with 2-chloro-N,N-dipropyl-acetamide (813 mg, 4.59 mmol) and sodium hydrogen carbonate (808 mg, 8.92 mmol). The reaction mixture was heated at 70° C. for 7 days. The reaction was allowed to cool to RT and diluted with water (100 ml). A white precipitate formed which was extracted into EtOAc (2×75 ml) and DCM (2×75 ml). The organic extracts were combined, dried over MgSO$_4$ and concentrated in vacuo to afford a brown oil. Purification by chromatography on silica eluting with a gradient of 0-20% EtOH/DCM afforded a yellow oily solid which was dissolved in DCM (~5 ml) and filtered through a 2 µM syringe filter. The solution was concentrated in vacuo to 1 ml, and diethyl ether (10 ml) was added. The resulting white precipitate was collected by filtration and dried in vacuo at 50° C. overnight to afford the title compound; $^1$H NMR (400 MHz, DMSO-d6) δ 9.10-7.94 (1H br), 8.43 (1H br s), 8.36 (1H, br s), 7.15 (2H, d), 6.96-6.45 (1H, br s), 6.86 (2H, d), 6.72 (2H, br s), 4.88 (2H, s), 4.81 (2H, s), 3.62-3.37 (4H, m), 1.67-1.54 (4H, m), 1.54-1.45 (4H, m), 0.85 (3H, t), 0.80 (3H, t). LC-MS Rt 4.45 mins; 672.5 [M+H]$^+$, Method 10minLC_v003.

Example 2.1

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid tert-butoxycarbonylmethyl ester

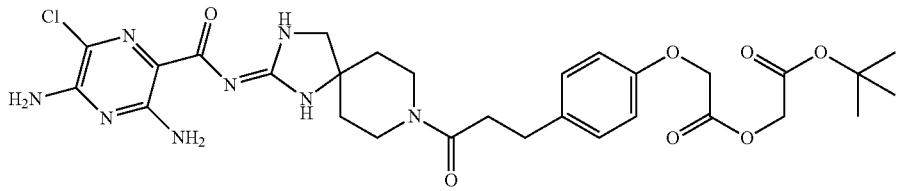 [SMILES: CC(C)(C)OC(=O)COC(=O)COc1ccc(CCC(=O)N2CCC3(CC2)CN/C(=N\C(=O)c2nc(Cl)c(N)nc2N)N3)cc1]

The title compound was prepared analogously to [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester (Ex. 2.0) by replacing 2-chloro-N,N-dipropyl-acetamide with t-butyl bromoacetate; $^1$H NMR (400 MHz, DMSO-d6) δ 8.45 (1H, br), 8.37 (1H, br), 7.16 (2H, d), 6.85 (2H, d), 6.8-6.6 (2H, br), 4.83 (2H, s), 4.64 (2H, s), 3.61 (1H, m), 3.58 (1H, m), 3.39 (2H, s), 3.38 (1H, m), 3.30 (1H, m), 2.75 (2H, t), 2.59 (2H, t), 1.60 (4H, m), 1.42 (9H, s). LC-MS Rt 4.27 mins; 645.3 [M+H]$^+$, Method 10minLC_v002.

The compounds of the following tabulated Examples (Table 2) were prepared by a similar method to that of Example 2.0 from [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid and the appropriate Intermediate (which are commercially available).

TABLE 2

| Ex. | Name | [M + H]$^+$/NMR |
|---|---|---|
| 2.2 | [4-(3-{2-[(E)-3,5-Diamino-6-chloro-pyrazine-2-carbonyl imino]-1,3,8-triaza-spiro[4.5]dec-8-yl}-3-oxo-propyl)-phenoxy]-acetic acid benzyloxycarbonylmethyl ester | 1H NMR (400 MHz, DMSO-d6) δ 8.50 (2H, b s), 7.38-7.31 (5H, m), 7.14 (2H, d), 6.84 (2H, d), 5.19 (2H, s), 4.87 (4H, s), 3.75-3.40 (4 H, m), 3.43 (2H, s), 2.75 (2H, t), 2.60 (2H, t), 1.63 (4H, m). LC-MS Rt 1.29 mins; 679.4[M + H]+ , Method 2 minLC_v002 |
| 2.3 | [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid diethylcarbamoylmethyl ester | 1H NMR (400 MHz, DMSO-d6) δ 8.50 (2H, b s), 7.16 (2H, d), 6.87 (2H, d), 4.88 (2H, s), 4.82 (2H, s), 3.75-3.55 (2H, m), 3.46 (2H, br s), 3.30-3.18 (4H, m, hidden by D2O peak), 2.76 (2H, t), 2.61 (2H, t), 1.64 (4H, br s), 1.12 (3H, t), 1.03 (3H, t). LC-MS Rt 1.13 mins; 644.5[M + H]+ , Method 2 minLC_v002. |
| 2.4 | [4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid 2-oxo-2-piperidin-1-yl-ethyl ester | $^1$H NMR (400 MHz, DMSO-d6) δ 8.63 (2H, br s), 7.16 (2H, d), 7.20-7.00 (2H, br s), 6.87 (2H, d), 4.91 (2H, s), 4.81 (2H, s), 3.69 (1H, m), 3.57 (1H, m), 3.46 (2H, s), 3.41 (2H, t), 3.40-3.00 (4H, hidden by D$_2$O peak), 2.75 (2H, t), 2.51 (2H, t), 1.63-1.43 (10H, m). LC-MS Rt 1.16 mins; 656.5 [M + H]$^+$, Method 2 minLC_v002. |

| Ex. | Structure |
|---|---|
| 2.2 | 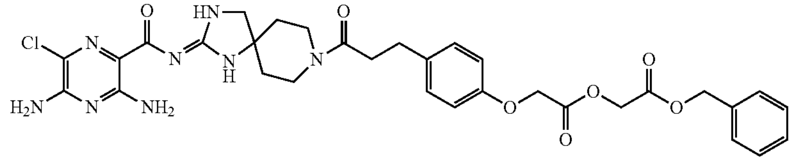 [SMILES: Nc1nc(N)c(C(=O)/N=C2\NCC3(CCN(C(=O)CCc4ccc(OCC(=O)OCC(=O)OCc5ccccc5)cc4)CC3)N2)nc1Cl] |
| 2.3 | 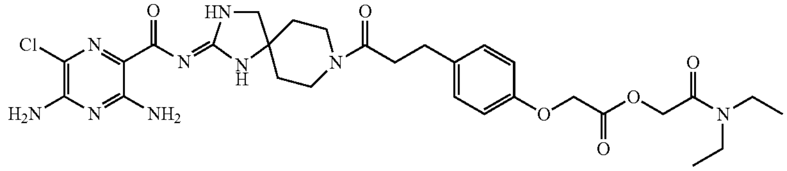 [SMILES: CCN(CC)C(=O)COC(=O)COc1ccc(CCC(=O)N2CCC3(CC2)CN/C(=N\C(=O)c2nc(Cl)c(N)nc2N)N3)cc1] |

| 2.4 | 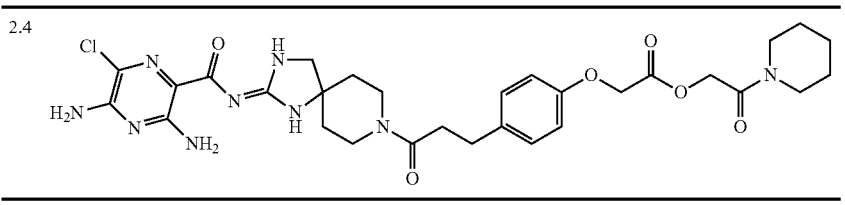 |
|---|---|

Example 3.0

[2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester with 4N HCl in dioxane (30 ml). The reaction mixture was stirred at RT for 24 h and filtered. The solid was washed with iso-hexane (300 ml) to afford the title compound as a hydrochloride salt;

$^1$H NMR (400 MHz, DMSO-d6) δ 11.00 (1H, s), 9.39 (1H, s), 9.07 (1H, s), 7.46 (2H, br s), 7.34 (1H, d), 7.14 (1H, dd),

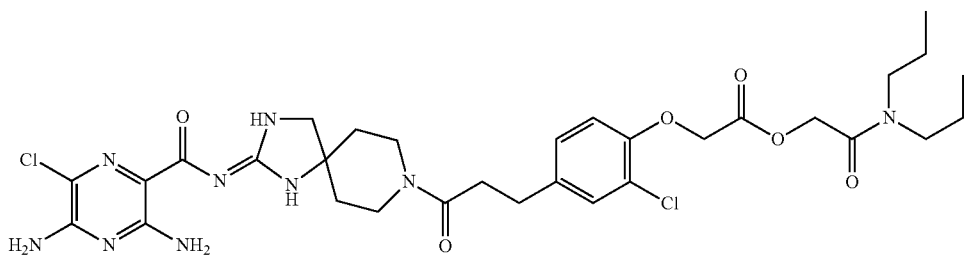 [SMILES: CCCN(CCC)C(=O)COC(=O)COc1ccc(CCC(=O)N2CCC3(CC2)CN/C(=N\C(=O)c2nc(Cl)c(N)nc2N)N3)cc1Cl]

Step 1: [2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid tert-butyl ester A stirred solution of 3-(4-tert-butoxycarbonylmethoxy-3-chloro-phenyl)-propionic acid (Intermediate B) (4 g, 12.71 mol) in DMF (80 ml) at RT was treated with HATU (4.83 g, 12.71 mmol), N-methylmorpholine (5.73 ml, 52.1 mmol) followed by 3,5-diamino-6-chloro-pyrazine-2-carboxylic acid [1,3,8-triaza-spiro[4.5]dec-(2E)-ylidene]-amide (WO09074575, Ex. 38, page 123) (5.31 g, 13.34 mmol). The resulting mixture was stirred at RT for 1 h and then diluted with water (500 ml). The resulting solid was collected by filtration and rinsed with water. Purification by chromatography on silica eluting with 0-7% 7N ammonia in MeOH/DCM afforded the title product; $^1$H NMR (400 MHz, DMSO-d6) δ 8.53 (2H, br hump), 7.34 (1H, d), 7.14 (1H, dd), 6.90 (1H, d), 6.87 (2H, br hump), 4.74 (2H, s), 3.65 (1H, m), 3.57 (1H, m), 3.43 (2H, s), 3.37 (2H, m), 2.75 (2H, t), 2.62 (2H, t), 1.62 (4H, m), 1.43 (9H, s).

LC-MS Rt 1.30 mins; 621.4 [M+H]$^+$, Method 2minLC_v002.

Step 2: [2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid

[2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid tert-butyl ester (step 1) (5.3 g, 8.53 mmol) was suspended in 1,4-dioxane (25 ml) and treated 6.92 (1H, d), 4.89 (2H, s), 3.83 (1H, m), 3.75 (1H, m), 3.70 (2H, s), 3.30 (1H, m), 3.16 (1H, m), 2.75 (2H, t), 2.64 (2H, t), 1.78 (4H, m). LC-MS Rt 1.10 mins; 565.3 [M+H]$^+$, Method 2minLC_v002.

Step 3: [2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester A solution of [2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid (step 2) (4.82 g, 8.52 mmol) in DMF (70 ml) was treated with 2-chloro-N,N-dipropyl-acetamide (3.18 g, 17.9 mmol) followed by sodium hydrogen carbonate (2.26 g, 26.9 mmol) and the resulting suspension heated to 60° C. overnight. Water (500 ml) was added to the reaction mixture and the product extracted with EtOAc (1000 ml). The organic extracts were washed with water (500 ml) and brine (500 ml), dried (MgSO$_4$) and concentrated in vacuo. Purification by chromatography on silica eluting with 0-12% 2N ammonia in ethanol in DCM followed by further purification by C18 reverse phase chromatography eluting with MeCN/water afforded the title product; $^1$H NMR (400 MHz, DMSO-d6) δ 8.43 (1H, br s), 8.36 (1H, br s), 7.34 (1H, d), 7.14 (1H, dd), 7.02 (1H, s), 6.71 (2H, br s), 4.95 (2H, s), 4.89 (2H, s), 3.67-3.53 (2H, m), 3.39 (3H, br s), 3.19 (2H, t), 3.13 (2H, t), 2.75 (2H, t), 2.62 (2H, t), 1.65-1.41 (8H, m), 0.85 (3H, t), 0.80 (3H, t). LC-MS Rt 4.11 mins; 706.5 [M+H]$^+$, Method 10minLC_v003.

Example 4

3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid 2-oxo-2-(2-trifluoromethyl-pyrrolidin-1-yl)-ethyl ester

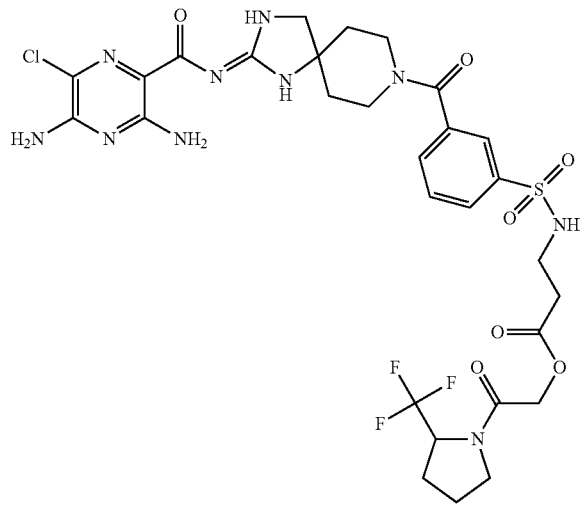 [SMILES: Nc1nc(N)c(C(=O)/N=C2\NCC3(CCN(C(=O)c4cccc(S(=O)(=O)NCCC(=O)OCC(=O)N5CCCC5C(F)(F)F)c4)CC3)N2)nc1Cl]

Step 1: 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid tert-butyl ester The title compound was prepared from 3-(2-tert-butoxycarbonyl-ethylsulfamoyl)-benzoic acid (Int. AD) and 3,5-diamino-6-chloro-pyrazine-2-carboxylic acid [1,3,8-triaza-spiro[4.5]dec-(2E)-ylidene]-amide hydrochloride in an analogous method to Example 1; LC-MS Rt 0.93 mins; 636.3 [M+H]⁺, Method 2minLC_v003.

Step 2: 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid A solution of 3-(3-{2-[(E)-3,5-diamino-6-chloro-pyrazine-2-carbonylimino]-1,3,8-triaza-spiro[4.5]decane-8-carbonyl}-benzenesulfonylamino)-propionic acid tert-butyl ester (step 1) (900 mg, 1.415 mmol) in 4N HCl in dioxane (10 ml) was stirred for 16 h at RT. Iso-hexane (10 ml) was added to the reaction mixture and resulting suspension was sonicated for 1 hour at RT. The solvent was decanted off and the solids washed with iso-hexane (10×25 ml). The resulting pale yellow crystals were dried under vacuum @45° C. for 36 h to afford the title compound; LC-MS Rt 0.80 mins; 580.0 [M+H]⁺, Method 2minLC_v003.

Step 3: 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid 2-oxo-2-(2-trifluoromethyl-pyrrolidin-1-yl)-ethyl ester To a stirred solution of 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid (step 2) (400 mg, 0.690 mmol) and N,N-diisopropylethylamine (357 mg, 2.76 mmol) in DMF (4 ml) was added HATU (262 mg, 0.690 mmol). The solution was stirred at RT for 15 min, after which time 2-hydroxy-1-(2-(trifluoromethyl)pyrrolidin-1-yl)ethanone (Int. D) (262 mg, 0.690 mmol) in DMF (2 ml) was added. The resulting solution was stirred at RT for 6 days, after which time it was poured onto water (10 ml). A white precipitate formed which was collected by filtration, and washed with iso-hexane (20 ml), and purified by C18 reverse phase chromatography eluting with MeCN/water/0.1% TFA to afford the title product; ¹H NMR (400 MHz, DMSO-d6) δ 11.03 (1H, s), 9.37 (1H, s), 9.02 (1H, s), 7.92-7.29 (4H, m), 7.24 (¹⁴N, s) 7.12 (¹⁴N, s), 6.96 (¹⁴N, s), 4.95-3.90 (11H, m), 3.66 (2H, t), 3.41 (2H, t), 3.35 (2H, m), 3.07 (2H, t) 2.20-1.61 (7H, m); LC-MS Rt 0.91 mins; 759.0 [M+H]⁺, Method 2minLC_v003.

Example 4.1

[2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid 2-(2-oxo-piperidin-1-yl)ethyl ester

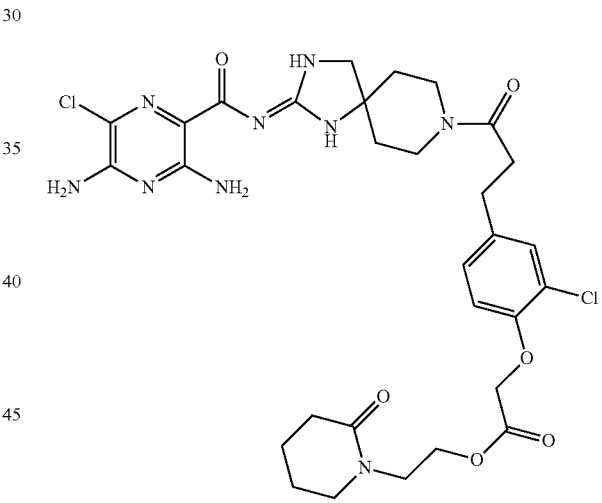

The title compound was prepared by an analogous method to Example 4.0, replacing 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid with [2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid (Ex. 3, step 2), and 2-hydroxy-1-(2-(trifluoromethyl)pyrrolidin-1-yl)ethanone (Int. D) with 1-(2-hydroxy-ethyl)piperidin-2-one;

¹H NMR (400 MHz, DMSO-D6) δ 11.1 (1H, s), 9.34 (1H, s), 9.06 (1H, s), 7.55-6.9 (4H, m), 4.84 (4H, s), 4.22 (2H, m), 3.95-3.41 (10H, m), 3.29 (2H, s), 2.77 (2H, m), 2.64 (2H, m), 2.59 (2H, m), 2.21 (2H, t), 1.88-1.59 (4H, m); LC-MS Rt 0.91 mins; 690.4 [M+H]⁺, Method 2minLC_v003.

Example 4.2

[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid 2-morpholin-4-yl-2-oxo-ethyl ester

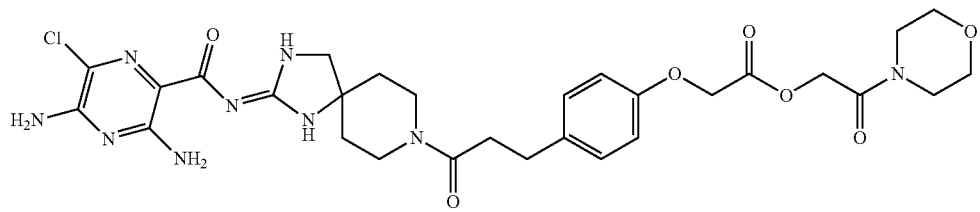 [SMILES: Nc1nc(N)c(C(=O)/N=C2\NCC3(CCN(C(=O)CCc4ccc(OCC(=O)OCC(=O)N5CCOCC5)cc4)CC3)N2)nc1Cl]

The title compound was prepared by an analogous method to Example 4.0, replacing 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid with [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid (Intermediate B), and 2-hydroxy-1-(2-(trifluoromethyl)pyrrolidin-1-yl)ethanone (Int. D) with 2-hydroxy-1-morpholin-4-yl-ethanone; $^1$H NMR (400 MHz, DMSO-d6) δ 8.40 (2H, br hump), 7.15 (2H, d), 6.87 (2H, d), 6.72 (2H, br s), 4.93 (2H, s), 4.82 (2H, s), 3.63 (2H, m), 3.56 (4H, m), 3.42 (2H, m), 3.40 (8H, m), 2.74 (2H, t), 2.59 (2H, t), 1.59 (4H, m). LC-MS Rt 3.10 mins; 658.4 [M+H]$^+$, Method 10minLC_v002.

Example 5.0

1-[(3-{2-[(E)-3,5-Diamino-6-chloro-pyrazine-2-carbonylimino]-1,3,8-triaza-spiro[4.5]decane-8-carbonyl}-benzenesulfonylamino)-methyl]-cyclobutanecarboxylic acid dipropylcarbamoylmethyl ester

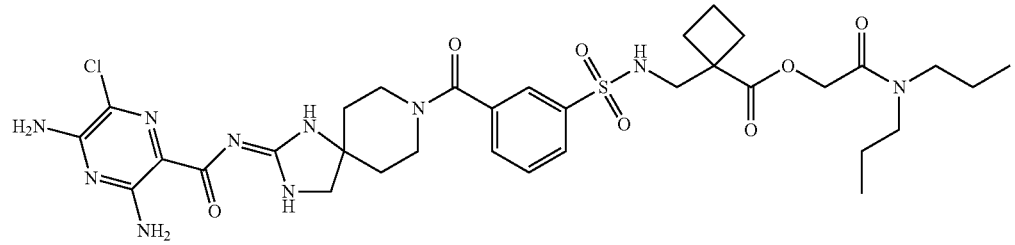 [SMILES: CCCN(CCC)C(=O)COC(=O)C1(CNS(=O)(=O)c2cccc(C(=O)N3CCC4(CC3)CN/C(=N\C(=O)c3nc(Cl)c(N)nc3N)N4)c2)CCC1]

Step 1: 1-[(3-{2-[(E)-3,5-Diamino-6-chloro-pyrazine-2-carbonylimino]-1,3,8-triaza-spiro[4.5]decane-8-carbonyl}-benzenesulfonylamino)-methyl]-cyclobutanecarboxylic acid tert-butyl ester A solution of 3-[(1-tert-butoxycarbonyl-cyclobutylmethyl)-sulfamoyl]-benzoic acid (Int. AC) (1.37 g, 3.71 mmol) in DMF (20 ml) was treated with N-methylmorpholine (1.631 ml, 14.83 mmol) and HATU (1.41 g, 3.71 mmol) followed by 3,5-diamino-6-chloro-pyrazine-2-carboxylic acid [1,3,8-triaza-spiro[4.5]dec-(2E)-ylidene]-amide (1.27 g, 3.89 mmol). The reaction mixture was stirred at RT for 2 h and then partitioned between EtOAc and water. The organic portion was separated and washed with 0.5M aqueous 1,5,7-triazabicyclo[4.4.0]dec-5-ene solution, brine, dried over MgSO$_4$ and concentrated in vacuo. Purification of the resulting oil by chromatography on silica eluting with 5-8% MeOH in isohexane afforded the title compound; LC-MS Rt 1.03 mins; 676.4 [M+H]$^+$, Method 2minLC_v003.

Step 2: 1-[(3-{2-[(E)-3,5-Diamino-6-chloro-pyrazine-2-carbonylimino]-1,3,8-triaza-spiro[4.5]decane-8-carbonyl}-benzenesulfonylamino)-methyl]-cyclobutanecarboxylic acid A suspension of 1-[(3-{2-[(E)-3,5-diamino-6-chloro-pyrazine-2-carbonylimino]-1,3,8-triaza-spiro[4.5]decane-8-carbonyl}-benzenesulfonylamino)-methyl]-cyclobutanecarboxylic acid tert-butyl ester (step 1) (730 mg, 1.080 mmol) in 4N HCl in dioxane (10 ml, 40.0 mmol) was stirred at RT for 1 h. The reaction mixture was partitioned between water and EtOAc and the pH of the aqueous portion was adjusted to 14 by addition of 2N NaOH. The basic aqueous solution was washed with EtOAc and concentrated in vacuo. The dry residue was slurried in water and the pH was adjusted to 6 by dropwise addition of 2N HCl. The resulting solid was filtered and washed with water (20 ml), diethyl ether (20 ml) and dried under vacuum at 50° C. to afford the title product; LC-MS Rt 2.29 mins; 620.3 [M+H]+, Method 10minLC_v003.

Step 3: 1-[(3-{2-[(E)-3,5-Diamino-6-chloro-pyrazine-2-carbonylimino]-1,3,8-triaza-spiro[4.5]decane-8-carbonyl}-benzenesulfonylamino)-methyl]-cyclobutanecarboxylic acid dipropylcarbamoylmethyl ester A solution of 1-[(3-{2-[(E)-3,5-diamino-6-chloro-pyrazine-2-carbonylimino]-1,3,8-triaza-spiro[4.5]decane-8-carbonyl}-benzenesulfonylamino)-methyl]-cyclobutanecarboxylic acid (step 2) (350 mg, 0.564 mmol) in DMF (10 ml) was stirred at 50° C. with pre-activated molecular sieves for 30 min. 2-Chloro-N,N-dipropylacetamide (100 mg, 0.564 mmol), sodium bicarbonate (142 mg, 1.693 mmol) and NaI (8.46 mg, 0.056 mmol) were added and stirring continued at 50° C. After 3.5 h, the mixture was allowed to cool to RT and the molecular sieves were removed. The mixture was poured into water and the resulting white suspension was filtered, washed with water and dried in vacuo. The solid was dissolved in DCM and diethyl ether was added to yield a white precipitate which was collected by filtration and dried under vacuum overnight to afford the title product; $^1$H NMR (400 MHz, DMSO-d6) δ 9.30-7.74 (4H, br hump), 7.88 (1H, d), 7.79 (1H, br s), 7.69 (1H, dd), 7.66 (1H, m), 7.11-6.67 (1H, br hump), 6.84-6.61 (2H, br s), 4.76 (2H, s), 3.82-3.29 (4H, m), 3.44 (2H, s), 3.18-3.14 (4H, m), 3.15 (2H, br s), 2.31-1.95 (4H, m), 1.81 (2H, m), 1.83-1.65 (4H, m), 1.54-1.45 (4H, m), 0.86 (3H, t), 0.80 (3H, t); LC-MS Rt 3.62 mins; 761.7 [M+H]+, Method 10minLC_v003.

Example 5.1

3-[3-(3-{2-[(E)-3,5-Diamino-6-chloro-pyrazine-2-carbonylimino]-1,3,8-triaza-spiro[4.5]decane-8-carbonyl}-phenyl)-ureido]-propionic acid dipropylcarbamoylmethyl ester

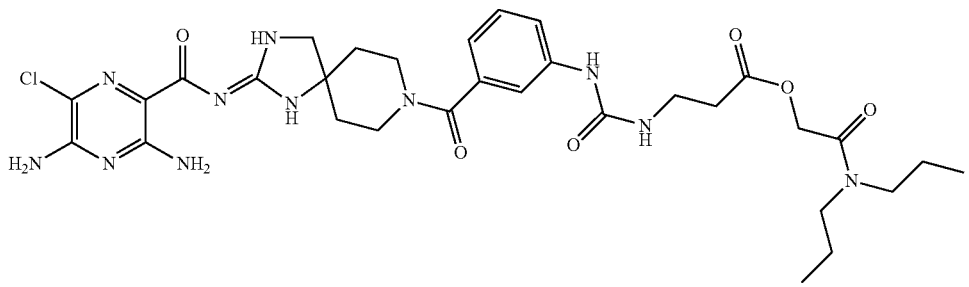 [SMILES: CCCN(CCC)C(=O)COC(=O)CCNC(=O)Nc1cccc(C(=O)N2CCC3(CC2)CN/C(=N\C(=O)c2nc(Cl)c(N)nc2N)N3)c1]

Step 1: 3-[3-(3-{2-[(E)-3,5-Diamino-6-chloro-pyrazine-2-carbonylimino]-1,3,8-triaza-spiro[4.5]decane-8-carbonyl}-phenyl)-ureido]-propionic acid ethyl ester The title compound was prepared from 3-[3-(2-ethoxycarbonyl-ethyl)-ureido]-benzoic acid (Int. F) and 3,5-diamino-6-chloro-pyrazine-2-carboxylic acid [1,3,8-triaza-spiro[4.5]dec-(2E)-ylidene]-amide hydrochloride using an analogous method to Example 1; LC-MS Rt 0.81 mins; 587.4 and 589.3 [M+H]+, Method 2minLC_v003.

Step 2: 3-[3-(3-{2-[(E)-3,5-Diamino-6-chloro-pyrazine-2-carbonylimino]-1,3,8-triaza-spiro[4.5]decane-8-carbonyl}-phenyl)-ureido]-propionic acid A solution of 3-[3-(3-{2-[(E)-3,5-diamino-6-chloro-pyrazine-2-carbonylimino]-1,3,8-triaza-spiro[4.5]decane-8-carbonyl}-phenyl)-ureido]-propionic acid ethyl ester (step 1) (2.17 g, 3.70 mmol) in THF (20 ml) was treated with LiOH (0.167 g, 4.07 mmol) and the reaction mixture was stirred at RT for 1 h. The mixture was partitioned between EtOAc and water and the aqueous portion was acidified to neutral pH and concentrated in vacuo. The residue was suspended in water (100 ml), and the resulting suspension was filtered, washed with cold water (100 ml) and dried to afford the title product; LC-MS Rt 0.73 mins; 559.3 [M+H]+, Method 2minLC_v003.

Step 3: 3-[3-(3-{2-[(E)-3,5-Diamino-6-chloro-pyrazine-2-carbonylimino]-1,3,8-triaza-spiro[4.5]decane-8-carbonyl}-phenyl)-ureido]-propionic acid dipropylcarbamoylmethyl ester The title compound was prepared by an analogous method Example 5.0 by replacing 1-[(3-{2-[(E)-3,5-diamino-6- chloro-pyrazine-2-carbonylimino]-1,3,8-triaza-spiro[4.5]
decane-8-carbonyl}-benzenesulfonylamino)-methyl]-cy-
clobutanecarboxylic acid (Ex. 4.0, step 3) with 3-[3-(3-{2-
[(E)-3,5-Diamino-6-chloro-pyrazine-2-carbonylimino]-1,3,
8-triaza-spiro[4.5]decane-8-carbonyl}-phenyl)-ureido]-
propionic acid (Ex. 5.1, step 2); $^1$H NMR (400 MHz, DMSO-
d6) δ 8.75 (1H, s), 8.50-8.40 (4H, br hump), 7.54 (1H, s), 7.30
(2H, m), 6.88 (1H, d), 6.72 (2H, br s), 6.31 (1H, t), 4.78 (2H,
s), 3.80-3.50 (4H, br humps), 3.43 (2H, s), 3.40 (2H, br s),
3.35-3.16 (4H, m), 2.56 (2H, t), 1.80-1.60 (4H, br m), 1.54-
1.45 (4H, m), 0.86 (3H, t), 0.80 (3H, t); LC-MS Rt 2.85mins;
700.5 [M+H]$^+$, Method 10minLC_v003.

Method A

Step 1: 3-Benzyloxycarbonylamino-propionic acid dipropylcarbamoylmethyl ester To a solution of benzyloxycarbonylamino-propionic acid
(22.3 g, 99.9 mmol) in DMF (150 ml) was added potassium The title compound may be prepared by either Method A or
B: carbonate (19.3 g, 139.9 mmol). 2-Chloro-N,N-dipropyl-
acetamide (17.7 g, 99.9 mmol) was added over 30 min, and
the reaction mixture was heated to 60° C. and stirred for 2.5 h.
The reaction mixture was allowed to cool to RT and diluted
with water (500 ml) and extracted with isopropyl acetate
(total 50 ml). The combined organic phases were washed with

Example 5.2

1-[(3-{2-[(E)-3,5-Diamino-6-chloro-pyrazine-2-car-
bonylimino]-1,3,8-triaza-spiro[4.5]decane-8-carbo-
nyl}-benzenesulfonylamino)-methyl]-cyclobutan-
ecarboxylic acid 2-oxo-2-(2-trifluoromethyl-
pyrrolidin-1-yl)-ethyl ester

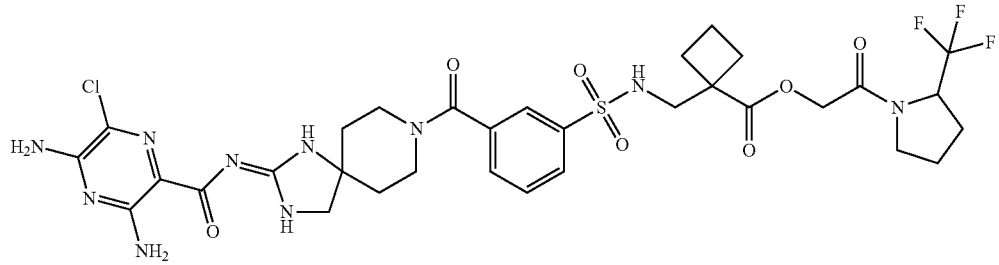 [SMILES: Nc1nc(N)c(C(=O)/N=C2\NCC3(CCN(C(=O)c4cccc(S(=O)(=O)NCC5(C(=O)OCC(=O)N6CCCC6C(F)(F)F)CCC5)c4)CC3)N2)nc1Cl]

The title compound was prepared by an analogous method
to that of Example 5.0 by replacing 2-chloro-N,N-dipropy-
lacetamide (Ex 5.0 step 3) with 2-chloro-1-(2-(trifluorom-
ethyl)pyrrolidin-1-yl)ethanone (Int. E); $^1$H NMR (400 MHz,
DMSO-d6) δ 8.54 (1H, br), 8.37 (1H, br), 7.89 (1H, m), 7.84
(1H, m), 7.79 (1H, m), 7.70 (1H, m), 6.73 (2H, br), 4.87 (1H,
m), 4.74 (2H, m), 3.82-3.36 (8H, br m), 3.70 (2H, m), 3.15
(2H, br s), 2.10-1.63 (12H, br m); LC-MS Rt 3.27 mins; 799.4
[M+H]$^+$, Method 10minLC_v003.

Preparation of Intermediate Compounds

Intermediate AA 3-(2-Dipropylcarbamoylmethoxycarbonyl-ethylsul-
famoyl)-benzoic acid

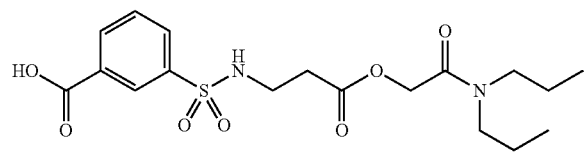 [SMILES: CCCN(CCC)C(=O)COC(=O)CCNS(=O)(=O)c1cccc(C(=O)O)c1]

water (3×200 ml) to afford a solution of 3-benzyloxycarbo-
nylamino-propionic acid dipropylcarbamoylmethyl ester in
isopropyl acetate which was not isolated further. LC-MS;
365.2 [M+H]$^+$ Method (i)

Step 2: 3-Amino-propionic acid dipropylcarbamoylmethyl ester trifluoroacetate A solution of 3-benzyloxycarbonylamino-propionic acid
dipropylcarbamoylmethyl ester in isopropyl acetate (33.2 g,
91.0 mmol in 129.9 g total mass of solution) was treated with
TFA (7.05 ml, 92.0 mmol) while the internal temperature was
maintained at 20° C., followed by 10% Pd/C (3.3 g, 50% wet)
and stirred under an atmosphere of H$_2$ (3 atm) for 3.5 h to
afford 3-amino-propionic acid dipropylcarbamoylmethyl
ester trifluoroacetate.

The solution was used directly in the next reaction without
isolation.

Step 3: Benzyl 3-(2-Dipropylcarbamoylmethoxycar-
bonyl-ethylsulfamoyl)-benzoic acid benzyl ester A solution of 3-amino-propionic acid dipropylcarbamoyl-
methyl ester trifluoroacetate (25.4 g 73.8 mmol) in isopropyl
acetate was cooled to 0° C. and treated with N-methylmor-
pholine (26.3 g, 221.5 mmol), water (40 ml) and DMAP (90.4
mg, 0.74 mmol). 3-Chlorosulfonyl-benzoic acid benzyl ester
(24.1 g, 77.5 mmol) in isopropyl acetate (44 ml) was added
and the reaction mixture was stirred for 2 h at 0-5° C. The
layers were separated and the organic phase was washed with
sat. aq. NaHCO$_3$ (3×26 ml), diluted with water (10 ml), the
pH adjusted to 6 with 1N HCl solution, and washed with brine. The resulting solution was concentrated to provide a solution of benzyl 3-(2-Dipropylcarbamoylmethoxycarbonyl-ethylsulfamoyl)-benzoic acid benzyl ester in isopropyl acetate which was used in further reactions without isolation. LC-MS; [M+H]⁺ 505.1 Method (i)

Step 4: Synthesis of 3-(2-Dipropylcarbamoyl-methoxycarbonyl-ethylsulfamoyl)-benzoic acid A solution of benzyl 3-(2-Dipropylcarbamoylmethoxycarbonyl-ethylsulfamoyl)-benzoic acid benzyl ester (5 g, 33.25 mmol) in isopropyl acetate (82 ml) was treated with 10% Pd/C (0.84 g, 50% wet), and stirred under H₂ (3 atm) overnight. The catalyst was removed by filtration. To the filtrate was added 10% Pd/C (1.68 g, 50% wet), and the reaction stirred under H₂ (3 atm) for 18 h. The catalyst was removed by filtration and further 10% Pd/C (1.68 g, 50% wet) was added and the reaction stirred under H₂ (1 atm) for 18 h. The catalyst was removed by filtration and washed with isopropyl acetate (20 ml). The combined filtrates were concentrated in vacuo and heptane was added to the solution and stirred at RT for 2 hr then −2° C. for 4 h. The solid which formed was collected by filtration and dried under vacuum at 40° C. to afford the title compound; LC-MS; 415.1 [M+H]⁺, Method (i).

Method B

Step 1: 3-tert-Butoxycarbonylamino-propionic acid dipropylcarbamoylmethyl ester

To a stirred suspension of Boc-Beta-Ala-OH (40.0 g, 211 mmol) in DMF (200 ml) at 60° C. under N₂ was added potassium carbonate (40.0 g, 289 mmol). To this mixture was added 2-chloro-N,N-dipropyl-acetamide (36.7 g, 207 mmol) in DMF (75 ml). The reaction mixture was allowed to stir at 60° C. overnight. The reaction was allowed to cool to RT and diluted with DCM (400 ml) followed by water (500 ml). The organic layer was separated and washed with brine (200 ml), dried over MgSO₄ and concentrated in vacuo to yield a pale yellow oil. To the oil was added n-heptane (500 ml) (azeotrope for DMF) which was concentrated in vacuo to afford the title compound; LC-MS Rt 1.14 mins; 331.3 [M+H]⁺, Method 2minLC_v003.

Step 2: 3-Amino-propionic acid dipropylcarbamoylmethyl ester

To a cooled stirred solution of 3-tert-butoxycarbonylamino-propionic acid dipropylcarbamoylmethyl ester (step 1) (36.5 g, 110 mmol) in dry dioxane under N₂ was added dropwise 4N HCl in dioxane (18.12 ml, 597 mmol). The resulting mixture was allowed to warm to RT and stirred overnight. The solvent was removed in vacuo and the crude product was suspended in EtOAc (500 ml) and sonicated for 1 h. The resulting white precipitate was isolated by filtration and was dried under vacuum at 40° C. for 1 h to afford a pale yellow solid. Recrystallisation from EtOAc afforded the title compound; LC-MS Rt 0.77 mins; 231.2 [M+H]⁺, Method 2minLC_v003.

Step 3: 3-(2-Dipropylcarbamoylmethoxycarbonyl-ethylsulfamoyl)-benzoic acid

To a stirred solution of 3-amino-propionic acid dipropylcarbamoylmethyl ester (step 2) (20.1 g, 75 mmol) in DCM (240 ml) at 0° C. under N₂ was added DMAP (0.46 g, 3.76 mmol) followed by TEA (38.8 ml, 278 mmol). The reaction mixture was treated with a solution of 3-chlorosulfonylbenzoic acid (16.6 g, 75 mmol) in DCM (200 ml). The mixture was allowed to stir at 0° C. for 1 h and then warmed up to RT for 1 h. Water (200 ml) was added and the pH adjusted with 1N HCl (100 ml). The organic layer was separated, dried over MgSO₄ and concentrated in vacuo. Purification by C18 reverse phase chromatography, eluting with MeCN/water (1% HCl) afforded the title product; LC-MS Rt 1.01 mins; 415.2 [M+H]⁺, Method 2minLC_v003.

Intermediate AB 3-(2-Cyclohexyloxycarbonylmethoxycarbonyl-ethylsulfamoyl)-benzoic acid

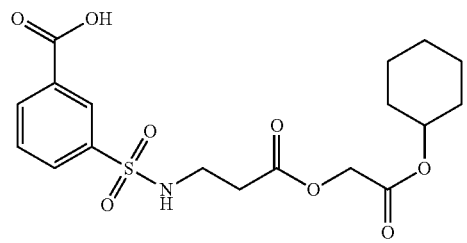 [SMILES: O=C(CCNS(=O)(=O)c1cccc(C(=O)O)c1)OCC(=O)OC1CCCCC1]

Step 1: 3-tert-Butoxycarbonylamino-propionic acid cyclohexyloxycarbonylmethyl ester This compound was prepared from cyclohexyl 2-chloroacetate and Boc-Beta-Ala-OH by an analogous method to 3-tert-butoxycarbonylamino-propionic acid dipropylcarbamoylmethyl ester (Int. AA step 1). Cesium carbonate was used in place of potassium carbonate; ¹H NMR (400 MHz, DMSO-d6) δ 6.83 (1H, br s), 4.76-4.70 (1H, m), 4.62 (2H, s), 3.20-3.12 (2H, m), 2.53 (2H, under DMSO peak), 1.28-1.72 (2H, m), 1.68-1.60 (2H, m), 1.53-1.18 (15H, m).

Step 2: 3-Amino-propionic acid cyclohexyloxycarbonylmethyl ester

The title compound was prepared from 3-tert-butoxycarbonylamino-propionic acid cyclohexyloxycarbonylmethyl ester (step 1) analogously to 3-amino-propionic acid dipropylcarbamoylmethyl ester (Int. AA, step 2); ¹H NMR (400 MHz, DMSO-d6) δ 7.86 (3H, br s), 4.76-4.71 (1H, m), 4.69 (2H, s), 3.04 (2H, m), 2.77 (2H, m), 1.82-1.75 (2H, m), 1.70-1.60 (2H, m), 1.53-1.19 (6H, m).

Step 3: 3-(2-Cyclohexyloxycarbonylmethoxycarbonyl-ethylsulfamoyl)-benzoic acid

A stirred solution of 3-amino-propionic acid cyclohexyloxycarbonylmethyl ester (step 2) (2.30 g, 10.03 mmol) in DCM (200 ml) at RT was treated with 3-chlorosulfonylbenzoic acid (3.64 g, 16.50 mmol) followed by N,N-diisopropylethylamine (3.04 ml, 17.45 mmol). The resulting mixture was stirred at RT for 1 h. The reaction mixture was washed with 2N HCl (200 ml), dried over MgSO₄ and concentrated in vacuo to afford the title compound; LC-MS Rt 1.34 mins; 414.2 [M+H]+, Method 2minLC_v002.

Intermediate AC

3-[(1-tert-Butoxycarbonyl-cyclobutylmethyl)-sulfamoyl]-benzoic acid

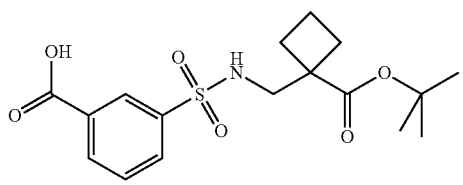 [SMILES: CC(C)(C)OC(=O)C1(CNS(=O)(=O)c2cccc(C(=O)O)c2)CCC1]

Step 1: 1-Cyano-cyclobutanecarboxylic acid tert-butyl ester

A solution of tert-butyl 2-cyanoacetate (4.0 g, 28.3 mmol), 1,3-dibromopropane (6.29 g, 31.2 mmol) in methyl ethyl ketone (100 ml) was treated with potassium carbonate (11.75 g, 85 mmol). The reaction mixture was heated to 80° C. for 17 h and then NaI (catalyst) (0.21 g, 1.42 mmol) was added. The mixture was heated at 80° C. for 6 days and then allowed to cool to RT. The mixture was filtered through Celite® (filter material) and the filtrate was concentrated in vacuo. Purification by chromatography on silica eluting with 10% EtOAc in iso-hexane afforded the title product as a colourless oil; $^1$H NMR (400 MHz, CDCl$_3$) δ 2.64 (4H, m), 2.22 (2H, m), 1.53 (9H, s).

Step 2: 1-Aminomethyl-cyclobutanecarboxylic acid tert-butyl ester

A suspension of Raney Ni (0.6 g, 13.19 mmol) in MeOH (30 ml) in a hydrogenation steel pressure vessel was treated with 1-cyano-cyclobutanecarboxylic acid tert-butyl ester (2.39 g, 13.19 mmol). The reaction mixture was placed under an atmosphere of hydrogen (3 bar) overnight. The mixture was filtered and concentrated in vacuo. The residue was dissolved in MeOH and passed through a 20 g Isolute® SCX-2 cartridge. The cartridge was washed with MeOH followed by product 7M ammonia in MeOH. The ammonia washings were concentrated in vacuo to afford the title product which was used without further purification. $^1$H NMR (400 MHz, CDCl$_3$) δ 2.45 (2H, m), 2.01-1.67 (6H, m), 0.49 (9H, s).

Step 3: 3-[(1-tert-Butoxycarbonyl-cyclobutylmethyl)-sulfamoyl]-benzoic acid methyl ester A solution of 1-aminomethyl-cyclobutanecarboxylic acid tert-butyl ester (step 2) (1.47 g, 7.38 mmol) in DCM (40 ml) was treated with TEA (2.57 ml, 18.44 mmol) followed by methyl 3-(chlorosulfonyl)benzoate (1.91 g, 8.11 mmol) and DMAP (0.09 g, 0.74 mmol). The mixture was stirred at RT for 2 h and then partitioned between DCM and water. The aqueous portion was extracted with DCM and the combined organic extracts were washed with 0.1N HCl, brine, dried over MgSO$_4$ and concentrated in vacuo. Purification of the resulting oil by chromatography on silica eluting with 0-40% EtOAc in iso-hexane afforded the title compound as a colourless oil; $^1$H NMR (400 MHz, CDCl$_3$) δ 8.56 (1H, s), 8.27 (1H, d), 8.08 (1H, d), 7.64 (1H, t), 5.21 (1H, br t), 3.98 (3H, s), 3.20 (2H, d), 2.37 (2H, m), 1.96 (4H, m), 1.46 (9H, s).

Step 4: 3-[(1-tert-Butoxycarbonyl-cyclobutylmethyl)-sulfamoyl]-benzoic acid A solution of 3-[(1-tert-butoxycarbonyl-cyclobutylmethyl)-sulfamoyl]-benzoic acid methyl ester (step 3) (1.87 g, 4.88 mmol) in THF (25 ml) was treated with 2M NaOH (aq) (24.38 ml, 48.8 mmol) and stirred at RT for 2 h. The reaction mixture was partitioned between diethyl ether and water. The aqueous portion was separated and acidified to pH 1 with 2N HCl, and extracted with EtOAc, and the combined organic portions were washed with brine, dried over MgSO$_4$ and concentrated in vacuo to afford the title product; $^1$H NMR (400 MHz, CDCl$_3$) δ 8.64 (1H, s), 8.33 (1H, d), 8.12 (1H, d), 7.67 (1H, t), 5.40 (1H, t), 3.24 (2H, d), 2.38 (2H, m), 1.97 (4H, m), 1.48 (9H, s). LC-MS Rt 1.13 mins; 314.1 [M+H]+ (-tBu), Method 2minLC_v003.

Intermediate AD 3-(2-tert-Butoxycarbonyl-ethylsulfamoyl)-benzoic acid

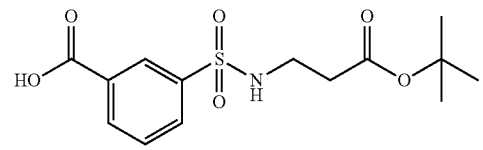 [SMILES: CC(C)(C)OC(=O)CCNS(=O)(=O)c1cccc(C(=O)O)c1]

Step 1: 3-(2-tert-Butoxycarbonyl-ethylsulfamoyl)-benzoic acid methyl ester

To a stirred solution of methyl 3-(chlorosulfonyl)benzoate (5.0 g, 21.31 mmol) in pyridine (50 ml), was added dropwise a solution of tert-butyl 3-aminopropanoate hydrochloride (5.11 g, 23.44 mmol) in pyridine (10 ml) at 0° C. The resulting solution was allowed to warm to RT and stirred for 4 h. 1N HCl (50 ml) was added to the reaction mixture and the aqueous phase was separated and extracted with DCM (3×20 ml). The combined organic fractions were dried (MgSO$_4$) and concentrated in vacuo to afford a viscous amber oil. Purification by chromatography on silica eluting with 0-100% EtOAc in iso-hexane afforded the title compound as a colourless oil. $^1$H NMR (400 MHz, CDCl$_3$) δ 8.53 (1H, s), 8.27 (1H, d), 8.08 (1H, d), 7.63 (1H, t) 5.38 (1H, t), 3.97 (3H, s), 3.20 (2H, m), 2.48 (2H, t), 1.43 (9H, s).

Step 2: 3-(2-tert-Butoxycarbonyl-ethylsulfamoyl)-benzoic acid

A solution of 3-(2-tert-Butoxycarbonyl-ethylsulfamoyl)-benzoic acid methyl ester (step 1) (5.0 g, 14.56 mmol) and lithium iodide (2.53 g, 18.93 mmol) in pyridine (60 ml) was heated at reflux for 16 h. The reaction mixture was concentrated in vacuo, diluted with DCM (60 ml) and poured into 1.5N HCl (60 ml). The aqueous phase was separated and extracted with DCM (6×60 ml). The combined organic extracts were dried (MgSO$_4$) and concentrated in vacuo. The crude residue was purified using an Isolute® PE-AX 10 g cartridge (anion exchange column), eluting with MeOH (200 ml) and then a 1:1 mixture of MeOH/AcOH (200 ml) to afford the title compound as white crystals; $^1$H NMR (400 MHz, CDCl$_3$) δ 8.63 (1H, s), 8.32 (1H, d), 8.14 (1H, d), 7.68 (1H, t), 5.63 (1H, t), 3.22 (2H, m), 2.51 (2H, t), 1.43 (9H, s).

Intermediate B 3-(4-tert-Butoxycarbonylmethoxy-3-chloro-phenyl)-propionic acid

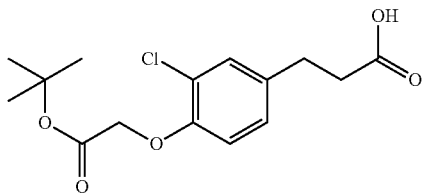 [SMILES: CC(C)(C)OC(=O)COc1ccc(CCC(=O)O)cc1Cl]

Step 1: 3-(3-Chloro-4-hydroxy-phenyl)-propionic acid benzyl ester

A solution of 3-(4-hydroxy-phenyl)-propionic acid benzyl ester (13.36 g, 52.1 mmol) in MeCN (100 ml) was cooled to 0° C. Trichloroisocyanuric acid (4.00 g, 17.2 mmol) was added, and the resulting white suspension was gradually allowed to warm to RT and stirred overnight. The reaction mixture was diluted with water (200 ml) and the product was extracted into EtOAc (250 ml) and dried (MgSO$_4$). Purification by chromatography on silica eluting with 0-20% EtOAc in iso-hexane afforded the title product; $^1$H NMR (400 MHz, DMSO-d6) δ 9.90 (1H, s), 7.32 (3H, m), 7.29 (2H, d), 7.18 (1H, d), 6.97 (1H, dd), 6.85 (1H, d), 5.07 (2H, s), 2.76 (2H, t), 2.64 (2H, t). LC-MS Rt 1.46 mins; 313.2 [M+H]$^+$, Method 2minLC_v002.

Step 2: 3-(4-tert-Butoxycarbonylmethoxy-3-chloro-phenyl)-propionic acid benzyl ester 3-(3-Chloro-4-hydroxy-phenyl)-propionic acid benzyl ester (step 1) (5.9 g, 20.3 mmol) in DMF (60 ml) was treated with potassium carbonate (5.61 g, 40.6 mmol) followed by t-butyl bromoacetate (4.49 ml, 30.4 mmol) and the mixture was heated at 60° C. overnight. The reaction mixture was diluted with water (500 ml), and the product extracted into EtOAc (450 ml). The organic portion was washed with water (200 ml), brine (200 ml), dried over MgSO$_4$ and the solvent removed in vacuo to yield a yellow oil. Purification by chromatography on silica eluting with 0-20% EtOAc in iso-hexane afforded the title product; $^1$H NMR (400 MHz, DMSO-d6) δ 7.34 (6H, m), 7.11 (1H, d), 6.89 (1H, d), 5.07 (2H, s), 4.74 (2H, s), 2.81 (2H, t), 2.68 (2H, t), 1.42 (9H, s). LC-MS Rt 1.64 mins; 427.3 [M+Na]$^+$, Method 2minLC_v002.

Step 3: 3-(4-tert-Butoxycarbonylmethoxy-3-chloro-phenyl)-propionic acid

A solution of 3-(4-tert-Butoxycarbonylmethoxy-3-chloro-phenyl)-propionic acid benzyl ester (step 2) (6.35 g, 15.7 mmol) in THF (60 ml) was added to a suspension of palladium on activated carbon (10% wt, 0.84 g, 0.78 mmol) in THF (35 ml) under an inert atmosphere. The resultant mixture was placed under an atmosphere of hydrogen (0.35 bar) for 3 h. The reaction mixture was filtered through Celite® (filter material) and washed through with THF (100 ml). The filtrate was concentrated in vacuo to afford the title compound as a yellow oil; $^1$H NMR (400 MHz, DMSO-d6) δ 12.15 (1H, s), 7.31 (1H, d), 7.12 (1H, dd), 6.91 (1H, d), 4.74 (2H, s), 2.75 (2H, t), 2.51 (2H, t), 1.38 (9H, s).

Intermediate CA 3-(4-{[(2-Hydroxy-ethyl-methyl-carbamoyl]-methoxycarbonylmethoxy}-phenyl)-propionic acid

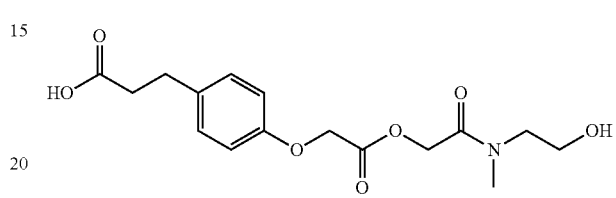

Step 1:
3-(4-tert-Butoxycarbonylmethoxy-phenyl)-propionic acid benzyl ester

This compound was prepared analogously to 3-(4-tert-butoxycarbonylmethoxy-3-chloro-phenyl)-propionic acid benzyl ester (Int. B step 2) by replacing 3-(3-chloro-4-hydroxy-phenyl)-propionic acid benzyl ester with 3-(4-hydroxy-phenyl)-propionic acid benzyl ester (commercially available).

Step 2: 3-(4-Carboxymethoxy-phenyl)-propionic acid benzyl ester 3-(4-tert-Butoxycarbonylmethoxy-phenyl)-propionic acid benzyl ester (step 1) (10 g, 27 mmol) in DCM (100 ml) was treated with TFA (20 ml) and heated at reflux for 4 h. The resulting mixture was concentrated in vacuo. The residue was dissolved in DCM and concentrated in vacuo a further four times until a viscous oil of the title compound was obtained.

Step 3: 3-(4-{[(2-Hydroxy-ethyl)-methyl-carbamoyl]-methoxycarbonylmethoxy}-phenyl)-propionic acid benzyl ester A mixture comprising 3-(4-carboxymethoxy-phenyl)-propionic acid benzyl ester (Step 2) (0.65 g, 1.93 mmol) and 2-chloro-N-(2-hydroxy-ethyl)-N-methyl-acetamide (0.35 g, 2.31 mmol) in DMF (10 ml) and sodium hydrogen carbonate (2.5 equivalents) was stirred at RT for 2 days and concentrated in vacuo. The crude residue was purified by chromatography on silica eluting with 0-5% MeOH in DCM to afford the title product as a viscous oil.

Step 4: 3-(4-{[(2-Hydroxy-ethyl)-methyl-carbamoyl]-methoxycarbonylmethoxy}-phenyl)-propionic acid A solution of 3-(4-{[(2-hydroxy-ethyl)-methyl-carbamoyl]-methoxycarbonylmethoxy}-phenyl)-propionic acid benzyl ester (step 3) (0.44 g, 1.02 mmol) in MeOH (20 ml) was treated with palladium on activated carbon (10% wt, 50 mg, 0.047 mmol) and stirred under an atmosphere of hydrogen for 20 h at RT. The reaction mixture was filtered through Celite® (filter material) and washed through with EtOAc. The filtrate was concentrated in vacuo and purification of the crude product by chromatography on silica eluting with 0-10% MeOH in DCM afforded the title compound; LC-MS: 340.2 [M+H]⁺.

Intermediate CB 3-(4-Cyclohexyloxycarbonylmethoxy-carbonylmethoxy-phenyl)-propionic acid This compound was prepared analogously to Intermediate CA by replacing 2-chloro-N-(2-hydroxy-ethyl)-N-methyl-acetamide (step 3) with chloro-acetic acid cyclohexyl ester; LC-MS: 363 [M+H]⁺.

Intermediate CC 3-(4-Dimethylcarbamoylmethoxycarbonylmethoxy-phenyl)-propionic acid LE This compound was prepared analogously to Intermediate CA by replacing 2-chloro-N-(2-hydroxy-ethyl)-N-methyl-acetamide (step 3) with 2-chloro-N,N-dimethyl acetamide; LC-MS: 400.2 [M+H]⁺.

Intermediate D

2-Hydroxy-1-(2-(trifluoromethyl)pyrrolidin-1-yl)ethanone

A solution of 2,2-dimethyl-1,3-dioxolan-4-one (0.57 g, 5.05 mmol) and (+/−)-2-(trifluoromethyl)pyrrolidine (1.0 g, 7.19 mmol) in PhMe (20 ml) was heated at reflux for 16 h.

The reaction mixture was poured into 1N HCl (20 ml) and DCM (20 ml). The aqueous phase was separated and extracted using DCM (3×20 ml) and the combined organic fractions dried (MgSO₄) and concentrated in vacuo to afford the title compound. ¹H NMR (400 MHz, CDCl₃) δ 4.83 (1H, m), 4.20 (2H, s), 3.5 (1H, m), 3.40 (1H, m), 3.22 (1H, s), 2.21 (2H, m), 2.10 (2H, m).

Intermediate E

2-Chloro-1-(2-(trifluoromethyl)pyrrolidin-1-yl)ethanone

A solution of 2-(trifluoromethyl)pyrrolidine (500 mg, 3.59 mmol) in DCM (10 ml) was treated with chloroacetyl chloride (0.31 ml, 3.77 mmol) and stirred at RT for 1 h. The resulting mixture was concentrated in vacuo to afford the title compound as a yellow oil which was used without further purification; ¹H NMR (400 MHz, CDCl₃) δ 4.84 (1H, m), 4.11 (2H, s), 3.71 (2H, m), 2.23 (2H, m), 2.07 (2H, m).

Intermediate F

3-[3-(2-Ethoxycarbonyl-ethyl)-ureido]-benzoic acid

A solution of 3-amino benzoic acid (5.0 g, 36.5 mmol) in THF (250 ml)/DCM (250 ml) was cooled to 0° C. and treated with triphosgene (3.79 g, 12.76 mmol) followed by TEA (12.70 ml, 91 mmol). After 5 min, a suspension of beta-alanine ethyl ester hydrochloride (11.20 g, 72.9 mmol) and TEA (12.70 ml, 91.00 mmol) in THF (10 ml)/DCM (10 ml) were added and the resulting mixture was allowed to warm to RT and stirred overnight. The reaction mixture was diluted with DCM (100 ml) and the pH was adjusted to 8 by addition of sat. aq. NaHCO₃. The mixture was extracted with water (2×250 ml). The combined aqueous extracts were acidified to pH 1 by addition of 2N HCl, extracted with DCM and the combined organic portions were washed with brine, dried over MgSO₄ and concentrated in vacuo to afford the title product as an off-white solid; LC-MS Rt 0.84 mins; 281.2 [M+H]⁺, Method 2minLC_v003.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EMBODIMENT

Consistory Clauses

Embodiment 1

A compound of Formula I:

or a pharmaceutically acceptable salt or solvate thereof, wherein $R^1$ is H, halogen, $C_1$-$C_8$-alkyl, $C_1$-$C_8$-haloalkoxy, $C_3$-$C_{15}$-carbocyclic group, nitro, cyano, a $C_6$-$C_{15}$-membered aromatic carbocyclic group, or a $C_1$-$C_8$-alkyl substituted by a $C_6$-$C_{18}$-membered aromatic carbocyclic group;

$R^2$, $R^3$, $R^4$ and $R^5$ are each independently selected from H and $C_1$-$C_6$ alkyl;

$R^6$, $R^7$, $R^8$ and $R^9$ are each independently selected from H; $SO_2R^{16}$; aryl optionally substituted by one or more Z groups; a $C_3$-$C_{10}$ carbocyclic group optionally substituted by one or more Z groups; $C_3$-$C_{14}$ heterocyclic group optionally substituted by one or more Z groups; $C_1$-$C_8$ alkyl optionally substituted by an aryl group which is optionally substituted by one or more Z groups, a $C_3$-$C_{10}$ carbocyclic group optionally substituted by one or more Z groups or a $C_3$-$C_{14}$ heterocyclic group optionally substituted by one or more Z groups;

$R^{10}$ is represented by the formula 2:

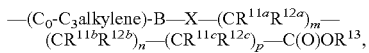
—($C_0$-$C_3$alkylene)-B—X—$(CR^{11a}R^{12a})_m$—$(CR^{11b}R^{12b})_n$—$(CR^{11c}R^{12c})_p$—C(O)O$R^{13}$, wherein the alkylene groups are optionally substituted by one or more Z groups;

B is aryl optionally substituted by one or more Z groups;

X is selected from a bond, —$NR^{15}(SO_2)$—, —$(SO_2)NR^{15}$—, —$(SO_2)$—, —$NR^{15}C(O)$—, —$C(O)NR^{15}$—, —$NR^{15}C(O)NR^{17}$—, —$NR^{15}C(O)O$—, —$NR^{15}$—, C(O)O, OC(O), C(O), O and S;

$R^{11a}$, $R^{11b}$, $R^{11c}$, $R^{12a}$, $R^{12b}$ and $R^{12c}$ are each independently selected from H and $C_1$-$C_6$ alkyl; or $R^{11a}$ and $R^{12a}$ together with the carbon atom to which they are attached form a 3- to 8-membered cycloalkyl group; or $R^{11b}$ and $R^{12b}$ together with the carbon atom to which they are attached form a 3- to 8-membered cycloalkyl group; or $R^{11c}$ and $R^{12c}$ together with the carbon atom to which they are attached form a 3- to 8-membered cycloalkyl group;

$R^{13}$ is selected from ($C_1$-$C_3$ alkyl)-C(O)N$R^{22}R^{23}$; ($C_1$-$C_3$ alkyl)-C(O)O$R^{23}$; and ($C_1$-$C_3$ alkyl)-N$R^{23}$C(O)$R^{22}$ $R^{15}$ and $R^{17}$ are each independently selected from H and $C_1$-$C_6$ alkyl;

$R^{16}$ is selected from $C_1$-$C_8$ alkyl, aryl and a 3- to 14-membered heterocyclic group, the heterocyclic group including one or more heteroatoms selected from N, O and S;

Z is independently selected from —OH, aryl, —O-aryl, $C_7$-$C_{14}$ aralkyl, —O—$C_7$-$C_{14}$ aralkyl, $C_1$-$C_6$ alkyl, $C_1$-$C_6$ alkoxy, —$NR^{19}(SO_2)R^{21}$, —$(SO_2)NR^{19}R^{21}$, —$(SO_2)R^{20}$, —$NR^{19}C(O)R^{20}$, —$C(O)NR^{19}R^{20}$, —$NR^{19}C(O)NR^2OR^{19}$, —$NR^{19}C(O)OR^{20}$, —$NR^{19}R^{21}$, C(O)O$R^{19}$, —C(O)$R^{19}$, S$R^{19}$, —O$R^{19}$, oxo, CN, $NO_2$, and halogen, wherein the alkyl, alkoxy, aralkyl and aryl groups are each optionally substituted by one or more substituents selected from OH, halogen, $C_1$-$C_4$ haloalkyl and $C_1$-$C_4$ alkoxy;

$R^{18}$, $R^{20}$ and $R^{22}$ are each independently selected from H and $C_1$-$C_6$ alkyl;

$R^{19}$, $R^{21}$ and $R^{23}$ are each independently selected from H; $C_1$-$C_6$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and —C(O)$C_1$-$C_6$ alkyl; —($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl and —C(O)$C_1$-$C_6$ alkyl; wherein the alkyl groups are optionally substituted by one or more halogen atoms, hydroxyl, $C_1$-$C_4$ alkoxy, —$C(O)NH_2$, —C(O)NH$C_1$-$C_6$ alkyl or —C(O)N($C_1$-$C_6$ alkyl)$_2$; or $R^{19}$ and $R^{20}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —$S(O)_2$-aryl; —$S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and C(O)O$C_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy; or $R^{19}$ and $R^{21}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —$S(O)_2$-aryl; —$S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and —C(O)O$C_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy; or $R^{18}$ and $R^{20}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —$S(O)_2$-aryl; —$S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and —C(O)O$C_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy; or $R^{22}$ and $R^{23}$ together with the atom(s) to which they are attached form a 5- to 10-membered heterocyclic group, the heterocyclic group including one or more further heteroatoms selected from N, O and S, the heterocyclic group being optionally substituted by one or more Z groups;

m is 0, 1, 2 or 3;

n is 0, 1, 2 or 3;

p is 0, 1, 2 or 3;

wherein at least one of m, n or p is not 0.

Embodiment 2

A compound according to embodiment 1, wherein $R^1$ is halogen.

Embodiment 3

A compound according to embodiment 1 or 2, wherein $R^2$, $R^3$, $R^4$ and $R^5$ are H.

Embodiment 4

A compound according to any preceding claim wherein $R^6$, $R^7$, $R^8$ and $R^9$ are H.

Embodiment 5

A compound according to any preceding claim wherein B is phenyl optionally substituted by halogen.

Embodiment 6

A compound according to any preceding claim wherein X is selected from —$(SO_2)NR^{15}$—, —$NR^{15}C(O)NR^{17}$—, and O.

Embodiment 7

A compound according to any preceding claim wherein $R^{11a}$, $R^{11b}$, $R^{11c}$, $R^{12a}$, $R^{12b}$ and $R^{12c}$ are each independently selected from H and $C_1$-$C_3$ alkyl; or
$R^{11a}$ and $R^{12a}$ together with the carbon atom to which they are attached form a 3, 4- or 5-membered cycloalkyl group; or
$R^{11b}$ and $R^{12b}$ together with the carbon atom to which they are attached form a 3, 4- or 5-membered cycloalkyl group; or
$R^{11c}$ and $R^{12c}$ together with the carbon atom to which they are attached form a 3, 4- or 5-membered cycloalkyl group.

Embodiment 8

A compound according to any preceding claim wherein the sum of m, n and p is 1, 2, or, 3.

Embodiment 9

A compound according to any preceding claim wherein $R^{13}$ is selected from ($C_1$ alkyl)-C(O)NR$^{22}$R$^{23}$; ($C_1$ alkyl)-C(O)OR$^{23}$; and ($C_2$ alkyl)-NR$^{23}$C(O)R$^{22}$

Embodiment 10

A compound according to any preceding claim wherein $R^{13}$ is selected from ($C_1$-$C_3$ alkyl)-C(O)NR$^{22}$R$^{23}$ and ($C_1$-$C_3$ alkyl)-C(O)OR$^{23}$; and wherein
$R^{22}$ is selected from H and $C_1$-$C_3$ alkyl;
$R^{23}$ is selected from H; $C_1$-$C_8$ alkyl; $C_3$-$C_8$ cycloalkyl; $C_1$-$C_4$ alkoxy-$C_1$-$C_4$ alkyl; ($C_0$-$C_4$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and C(O)$C_1$-$C_8$ alkyl; ($C_0$-$C_4$ alkyl)-O-aryl optionally substituted by one or more groups selected from $C_1$-$C_6$ alkyl, $C_1$-$C_6$ alkoxy and halogen; and ($C_0$-$C_4$ alkyl)-O-3- to 14-membered heterocyclic group, the heterocyclic group including one or more heteroatoms selected from N, O and S, optionally substituted by one or more groups selected from halogen, $C_1$-$C_6$ alkyl and C(O)$C_1$-$C_8$ alkyl; wherein the alkyl groups are optionally substituted by one or more halogen atoms, hydroxyl $C_1$-$C_4$ alkoxy, C(O)NH$_2$, C(O)NHC$_1$-$C_6$ alkyl or C(O)N($C_1$-$C_8$ alkyl)$_2$; or
$R^{22}$ and $R^{23}$ together with the nitrogen to which they are attached form a 5- to 7-membered heterocycloalkyl group, the heterocycloalkyl group including one or more further heteroatoms selected from N, O and S, the heterocycloalkyl group being optionally substituted by one or more Z groups.

Embodiment 11

A compound according to any of embodiments 1 to 9 wherein $R^{13}$ is ($C_1$-$C_3$ alkyl)-NR$^{23}$C(O)R$^{22}$, and wherein $R^{22}$ and $R^{23}$ together with the atoms to which they are attached form an oxo substituted 5- to 7-membered heterocycloalkyl group, the heterocycloalkyl group including one or more further heteroatoms selected from N, O and S, the heterocycloalkyl group being optionally further substituted by one or more Z groups.

Embodiment 12

A compound according to any preceding claim which is a compound of Formula Ia

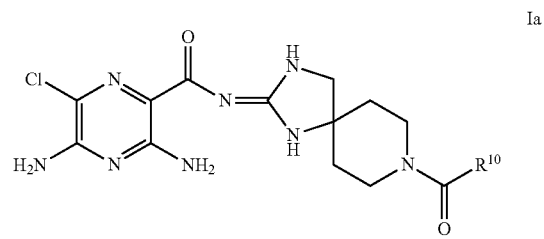

Ia or a pharmaceutically acceptable salt or solvate thereof wherein $R^{10}$ is as defined in any preceding claim.

Embodiment 13

A compound according to any preceding embodiment which is a compound of Formula Ib

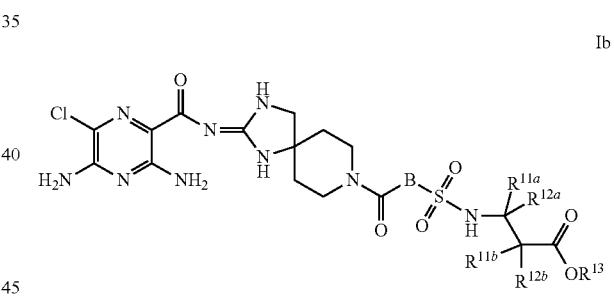

Ib or a pharmaceutically acceptable salt thereof wherein B, $R^{11a}$, $R^{12a}$, $R^{11b}$, $R^{12b}$ and $R^{13}$ are as defined anywhere above in respect of a compound of Formula I.

Embodiment 14

A compound according to embodiments 1 to 12 which is a compound of Formula Ic

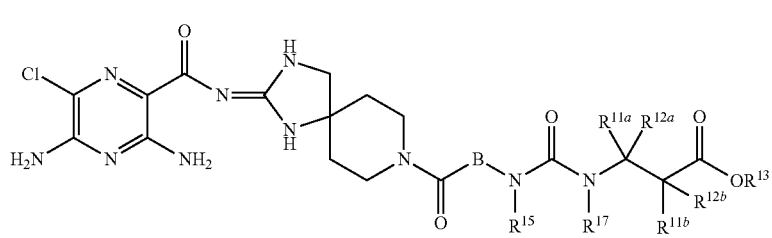

Ic or a pharmaceutically acceptable salt or solvate thereof wherein B, $R^{11a}$, $R^{12a}$, $R^{11b}$, $R^{12b}$, $R^{13}$ and $R^{15}$ and $R^{17}$ are as defined anywhere above in respect of a compound of Formula I.

Embodiment 15

A compound according to embodiments 1 to 12 which is a compound of Formula I

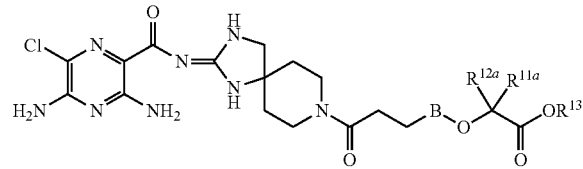

Id or a pharmaceutically acceptable salt or solvate thereof wherein B, $R^{11a}$, $R^{12a}$, and $R^{13}$ are as defined anywhere above in respect of a compound of Formula I.

Embodiment 16

A compound according to embodiment 1 selected from:
3-(3-{2-[(E)-3,5-Diamino-6-chloro-pyrazine-2-carbonylimino]-1,3,8-triaza-spiro[4.5]decane-8-carbonylyl}-benzenesulfonylamino)-propionic acid dipropylcarbamoylmethyl ester;
[4-(3-{2-[(Z)-3,5-Diamino-6-chloro-pyrazine-2-carbonylimino]-1,3,8-triaza-spiro[4.5]dec-8-yl}-3-oxo-propyl)-phenoxy]-acetic acid [(2-hydroxy-ethyl)-methyl-carbamoyl]-methyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid cyclohexyl oxycarbonylmethyl ester;
3-(3-{2-[(E)-3,5-Diamino-6-chloro-pyrazine-2-carbonylimino]-1,3,8-triaza-spiro[4.5]decane-8-carbonyl}-benzene sulfonylamino)-propionic acid cyclohexyloxy carbonylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dimethylcarbamoylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid tert-butoxycarbonylmethyl ester;
[4-(3-{2-[(E)-3,5-Diamino-6-chloro-pyrazine-2-carbonyl imino]-1,3,8-triaza-spiro[4.5]dec-8-yl}-3-oxo-propyl)-phenoxy]-acetic acid benzyloxycarbonylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid diethylcarbamoylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid 2-oxo-2-piperidin-1-yl-ethyl ester;
[2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester;
3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid 2-oxo-2-(2-trifluoromethyl-pyrrolidin-1-yl)-ethyl ester;
[2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid 2-(2-oxo-piperidin-1-yl)-ethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid 2-morpholin-4-yl-2-oxo-ethyl ester;
1-[(3-{2-[(E)-3,5-Diamino-6-chloro-pyrazine-2-carbonylimino]-1,3,8-triaza-spiro[4.5]decane-8-carbonyl}-benzenesulfonylamino)-methyl]-cyclobutanecarboxylic acid dipropylcarbamoylmethyl ester;
3-[3-(3-{2-[(E)-3,5-Diamino-6-chloro-pyrazine-2-carbonylimino]-1,3,8-triaza-spiro[4.5]decane-8-carbonyl}-phenyl)-ureido]-propionic acid dipropylcarbamoylmethyl ester; and
1-[(3-{2-[(E)-3,5-Diamino-6-chloro-pyrazine-2-carbonylimino]-1,3,8-triaza-spiro[4.5]decane-8-carbonyl}-benzenesulfonylamino)-methyl]-cyclobutanecarboxylic acid 2-oxo-2-(2-trifluoromethyl-pyrrolidin-1-yl)-ethyl ester;

or a pharmaceutically acceptable salt or solvate thereof.

Embodiment 17

A compound according to embodiment 16 selected from:
3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester; and
[2-Chloro-4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester;

or a pharmaceutically acceptable salt or solvate thereof.

Embodiment 18

A pharmaceutical composition, comprising:
a compound according to any of embodiments 1 to 16 and
one or more pharmaceutically acceptable excipients, diluents and/or carriers.

Embodiment 19

A pharmaceutical composition according to embodiment 18, comprising:
one or more other therapeutic agents.

Embodiment 20

A pharmaceutical composition according to claim 15, comprising
a second agent, wherein the second agent is a CFTR potentiator of formula

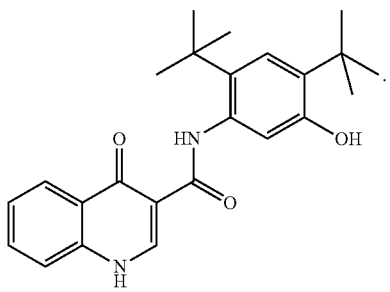 [SMILES: CC(C)(C)c1cc(C(C)(C)C)c(NC(=O)c2c[nH]c3ccccc3c2=O)cc1O]

Embodiment 21

A compound according to embodiments 1 to 17 for use in treating or preventing a disease or condition mediated by blockade of the epithelial sodium channel.

Embodiment 22

A compound according to embodiment 21, wherein the disease or condition is cystic fibrosis or COPD.

Embodiment 23

A compound according to embodiment 22, wherein the disease or condition is cystic fibrosis.

Embodiment 24

Use of a compound according to any of embodiments 1 to 17 in the manufacture of a medicament for the prevention or treatment of a disease or condition mediated by blockade of the epithelial sodium channel

Embodiment 25

A method for preventing or treating a disease or condition mediated by blockade of the epithelial sodium channel in which an effective amount of a compound according to any of embodiments 1 to 17 is administered to a patient in need of such treatment.

Embodiment 26

A process for preparing a compound of formula I or a pharmaceutically acceptable salt or solvate thereof comprising the step of:

(a). reacting a compound of formula II

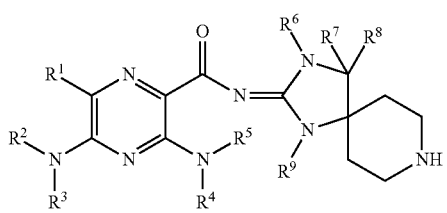

wherein $R^1$, $R^2$, $R^3$, $R^4$, $R^5$, $R^6$, $R^7$, $R^8$ and $R^9$ are as defined in any of embodiments 1 to 9, with a compound of formula III under convention reaction conditions for acid-amine coupling

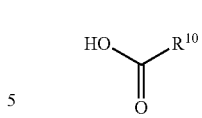

wherein $R^1$, $R^2$, $R^3$, $R^4$, $R^5$, $R^6$, $R^7$, $R^8$, $R^9$ and $R^{10}$ are as defined in any of embodiments 1 to 9; or (b) reacting a compound of formula IV

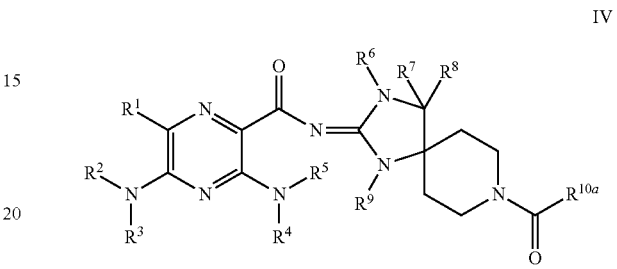

with a compound $R^{13}$-L of formula V under convention reaction conditions wherein $R^1$, $R^2$, $R^3$, $R^4$, $R^5$, $R^6$, $R^7$, $R^8$, $R^9$ and $R^{13}$ are as defined in any of embodiments;

$R^{10a}$ is $—(C_0-C_3\text{alkylene})-B—X—(CR^{11a}R^{12a})_m—(CR^{11b}R^{12b})_n—(CR^{11c}R^{12c})_p—C(O)OH$ wherein B, X, $R^{11a}$, $R^{11b}$, $R^{11c}$, $R^{12a}$, $R^{12b}$, $R^{12c}$, m, n, and p are as defined in any of claims 1 to 9; and L is a leaving group.

The invention claimed is:
1. A compound of Formula I:

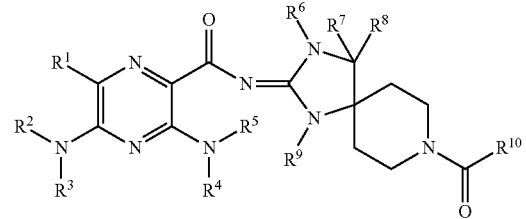

or a pharmaceutically acceptable salt thereof, wherein
$R^1$ is H, halogen, $C_1$-$C_8$-alkyl, $C_1$-$C_8$-haloalkyl, $C_1$-$C_8$-haloalkoxy, $C_3$-$C_{15}$-carbocyclic group, nitro, cyano, a $C_6$-$C_{15}$-membered aromatic carbocyclic group, or a $C_1$-$C_8$-alkyl substituted by a $C_6$-$C_{15}$-membered aromatic carbocyclic group;
$R^2$, $R^3$, $R^4$ and $R^5$ are each independently selected from H and $C_1$-$C_6$ alkyl;
$R^6$, $R^7$, $R^8$ and $R^9$ are each independently selected from H; $SO_2R^{16}$; aryl optionally substituted by one or more Z groups; a $C_3$-$C_{10}$ carbocyclic group optionally substituted by one or more Z groups; $C_3$-$C_{14}$ heterocyclic group optionally substituted by one or more Z groups; $C_1$-$C_8$ alkyl optionally substituted by an aryl group which is optionally substituted by one or more Z groups;
$R^{10}$ is represented by the formula 2:
$—(C_0-C_3\text{alkylene})-B—X—(CR^{11a}R^{12a})_m—(CR^{11b}R^{12b})_n—(CR^{11c}R^{12c})_p—C(O)OR^{13}$,
wherein the alkylene groups are optionally substituted by one or more Z groups;
B is aryl optionally substituted by one or more Z groups;

X is selected from a bond, —$NR^{15}(SO_2)$—, —$(SO_2)NR^{15}$—, —$(SO_2)$—, —$NR^{15}C(O)$—, —$C(O)NR^{15}$—, —$NR^{15}C(O)NR^{17}$—, —$NR^{15}C(O)O$—, —$NR^{15}$—, $C(O)O$, $OC(O)$, $C(O)$, O and S; $R^{11a}$, $R^{11b}$, $R^{11c}$, $R^{12a}$, $R^{12c}$ are each independently selected from H and $C_1$-$C_6$ alkyl; or $R^{11a}$ and $R^{12a}$ together with the carbon atom to which they are attached form a 3- to 8-membered cycloalkyl group; or $R^{11b}$ and $R^{12b}$ together with the carbon atom to which they are attached form a 3- to 8-membered cycloalkyl group; or $R^{11c}$ and $R^{12c}$ together with the carbon atom to which they are attached form a 3- to 8-membered cycloalkyl group;

$R^{13}$ is selected from ($C_1$-$C_3$ alkyl)-$C(O)NR^{22}R^{23}$; ($C_1$-$C_3$ alkyl)-$C(O)OR^{23}$; and ($C_1$-$C_3$ alkyl)-$NR^{23}C(O)R^{22}$ $R^{15}$ and $R^{17}$ are each independently selected from H and $C_1$-$C_6$ alkyl;

$R^{16}$ is selected from $C_1$-$C_8$ alkyl, aryl and a 3- to 14-membered heterocyclic group, the heterocyclic group including one or more heteroatoms selected from N, O and S;

Z is independently selected from —OH, aryl, —O-aryl, $C_7$-$C_{14}$ aralkyl, —O—$C_7$-$C_{14}$ aralkyl, $C_1$-$C_6$ alkyl, $C_1$-$C_6$ alkoxy, —$NR^{19}(SO_2)R^{21}$, —$(SO_2)NR^{19}R^{21}$, —$(SO_2)R^{20}$, —$NR^{19}C(O)R^{20}$, —$C(O)NR^{19}R^{20}$, —$NR^{19}C(O)NR^{20}R^{18}$, —$NR^{19}C(O)OR^{20}$, —$NR^{19}R^{21}$, $C(O)OR^{19}$, —$C(O)R^{19}$, $SR^{19}$, —$OR^{19}$, oxo, CN, $NO_2$, and halogen, wherein the alkyl, alkoxy, aralkyl and aryl groups are each optionally substituted by one or more substituents selected from OH, halogen, $C_1$-$C_4$ haloalkyl and $C_1$-$C_4$ alkoxy;

$R^{18}$, $R^{20}$ and $R^{22}$ are each independently selected from H and $C_1$-$C_6$ alkyl;

$R^{19}$, $R^{21}$ and $R^{23}$ are each independently selected from H; $C_1$-$C_8$ alkyl; $C_3$-$C_8$ cycloalkyl; $C_1$-$C_4$ alkoxy-$C_1$-$C_4$ alkyl; ($C_0$-$C_a$ alkyl)-aryl optionally substituted by one or more groups selected from $C_1$-$C_6$ alkyl, $C_1$-$C_6$ alkoxy and halogen; ($C_0$-$C_4$ alkyl)-3- to 14-membered heterocyclic group, the heterocyclic group including one or more heteroatoms selected from N, O and S, optionally substituted by one or more groups selected from halogen, oxo, $C_1$-$C_6$ alkyl and —$C(O)C_1$-$C_6$ alkyl; —($C_0$-$C_4$ alkyl)-O-aryl optionally substituted by one or more groups selected from $C_1$-$C_6$ alkyl, $C_1$-$C_6$ alkoxy and halogen; and ($C_0$-$C_a$ alkyl)-O-3- to 14-membered heterocyclic group, the heterocyclic group including one or more heteroatoms selected from N, O and S, optionally substituted by one or more groups selected from halogen, $C_1$-$C_6$ alkyl and —$C(O)C_1$-$C_6$ alkyl; wherein the alkyl groups are optionally substituted by one or more halogen atoms, hydroxyl, $C_1$-$C_4$ alkoxy, —$C(O)NH_2$, —$C(O)NHC_1$-$C_6$ alkyl or —$C(O)N(C_1$-$C_6$ alkyl$)_2$; or $R^{19}$ and $R^{20}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —$S(O)_2$-aryl; —$S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and $C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy; or $R^{19}$ and $R^{21}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —$S(O)_2$-aryl; —$S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and —$C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy; or $R^{18}$ and $R^{20}$ together with the nitrogen atom to which they are attached form a 5- to 10-membered heterocyclic group, the heterocyclic group including one or more further heteroatoms selected from N, O and S, the heterocyclic group being optionally substituted by one or more substituents selected from OH; halogen; aryl; 5- to 10-membered heterocyclic group including one or more heteroatoms selected from N, O and S; —$S(O)_2$-aryl; —$S(O)_2$—$C_1$-$C_6$ alkyl; $C_1$-$C_6$ alkyl optionally substituted by one or more halogen atoms; $C_1$-$C_6$ alkoxy optionally substituted by one or more OH groups or $C_1$-$C_4$ alkoxy; and —$C(O)OC_1$-$C_6$ alkyl, wherein the aryl and heterocyclic substituent groups are themselves optionally substituted by $C_1$-$C_6$ alkyl, $C_1$-$C_6$ haloalkyl or $C_1$-$C_6$ alkoxy; or $R^{22}$ and $R^{23}$ together with the atom(s) to which they are attached form a 5- to 10-membered heterocyclic group, the heterocyclic group including one or more further heteroatoms selected from N, O and S, the heterocyclic group being optionally substituted by one or more Z groups;

m is 0, 1, 2 or 3;
n is 0, 1, 2 or 3;
p is 0, 1, 2 or 3;
wherein at least one of m, n or p is not 0.

2. A compound according to claim 1, or a pharmaceutically acceptable salt thereof, wherein
$R^1$ is halogen;
$R^2$, $R^3$, $R^4$ and $R^5$ are H; and
$R^6$, $R^7$, $R^8$ and $R^9$ are H.

3. A compound according to claim 1, or a pharmaceutically acceptable salt thereof, wherein B is phenyl optionally substituted by halogen.

4. A compound according to claim 1, or a pharmaceutically acceptable salt thereof, wherein X is selected from —$(SO_2)NR^{15}$—, —$NR^{15}C(O)NR^{17}$—, and O.

5. A compound according to claim 1, or a pharmaceutically acceptable salt thereof, wherein $R^{11a}$, $R^{11b}$, $R^{11c}$, $R^{12a}$, $R^{12b}$ and $R^{12c}$ are each independently selected from H and $C_1$-$C_3$ alkyl; or $R^{11a}$ and $R^{12a}$ together with the carbon atom to which they are attached form a 3,4- or 5-membered cycloalkyl group; or
$R^{11b}$ and $R^{12b}$ together with the carbon atom to which they are attached form a 3,4- or 5-membered cycloalkyl group; or
$R^{11c}$ and $R^{12c}$ together with the carbon atom to which they are attached form a 3,4- or 5-membered cycloalkyl group.

6. A compound according to claim 1, or a pharmaceutically acceptable salt thereof, wherein the sum of m, n and p is 1, 2, or 3.

7. A compound according to claim 1, or a pharmaceutically acceptable salt thereof, wherein $R^{13}$ is selected from $(C_1-C_3$ alkyl)-C(O)NR$^{22}$R$^{23}$ and $(C_1-C_3$ alkyl)-C(O)OR$^{23}$; and wherein
$R^{22}$ is selected from H and $C_1-C_3$ alkyl;
$R^{23}$ is selected from H; $C_1-C_8$ alkyl; $C_3-C_8$ cycloalkyl; $C_1-C_4$ alkoxy-$C_1-C_4$ alkyl; $(C_0-C_4$ alkyl)-aryl optionally substituted by one or more groups selected from $C_1-C_6$ alkyl, $C_1-C_6$ alkoxy and halogen; $(C_0-C_4$ alkyl)-3- to 14-membered heterocyclic group, the heterocyclic group including one or more heteroatoms selected from N, O and S, optionally substituted by one or more groups selected from halogen, oxo, $C_1-C_6$ alkyl and C(O)C$_1-C_6$ alkyl; $(C_0-C_a$ alkyl)-O-aryl optionally substituted by one or more groups selected from $C_1-C_6$ alkyl, $C_1-C_6$ alkoxy and halogen; and $(C_0-C_4$ alkyl)-O-3- to 14-membered heterocyclic group, the heterocyclic group including one or more heteroatoms selected from N, O and S, optionally substituted by one or more groups selected from halogen, $C_1-C_6$ alkyl and C(O)C$_1-C_6$ alkyl; wherein the alkyl groups are optionally substituted by one or more halogen atoms, hydroxyl $C_1-C_4$ alkoxy, C(O)NH$_2$, C(O)NHC$_1-C_6$ alkyl or C(O)N(C$_1-C_6$ alkyl)$_2$; or
$R^{22}$ and $R^{23}$ together with the nitrogen to which they are attached form a 5- to 7-membered heterocycloalkyl group, the heterocycloalkyl group including one or more further heteroatoms selected from N, O and S, the heterocycloalkyl group being optionally substituted by one or more Z groups.

8. A compound according to claim 1, which is a compound of Formula Ia

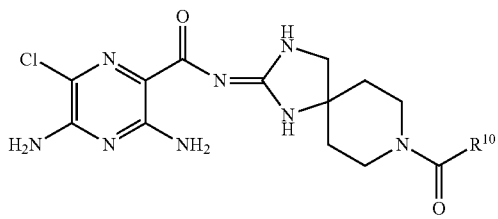

Ia or a pharmaceutically acceptable salt thereof.

9. A compound according to claim 1 selected from the group consisting of:
3-(3-{2-[(E)-3,5-Diamino-6-chloro-pyrazine-2-carbonylimino]-1,3,8-triaza-spiro[4.5]decane-8-carbonyly}-benzenesulfonylamino)-propionic acid dipropylcarbamoylmethyl ester;
[4-(3-{2-[(Z)-3,5-Diamino-6-chloro-pyrazine-2-carbonylimino]-1,3,8-triaza-spiro[4.5]dec-8-yl}-3-oxo-propyl)-phenoxy]acetic acid [(2-hydroxy-ethyl)-methyl-carbamoyl]-methyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid cyclohexyl oxycarbonylmethyl ester;
3-(3-{2-[(E)-3,5-Diamino-6-chloro-pyrazine-2-carbonylimino]-1,3,8-triaza-spiro[4.5]decane-8-carbonyly}-benzene sulfonylamino)-propionic acid cyclohexyloxy carbonylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid dimethylcarbamoylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid tert-butoxycarbonylmethyl ester;
[4-(3-{2-[(E)-3,5-Diamino-6-chloro-pyrazine-2-carbonyl imino]-1,3,8-triaza-spiro[4.5]dec-8-yl}-3-oxo-propyl)-phenoxy]-acetic acid benzyloxycarbonylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid diethylcarbamoylmethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid 2-oxo-2-piperidin-1-yl-ethyl ester;
3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid 2-oxo-2-(2-trifluoromethyl-pyrrolidin-1-yl)-ethyl ester;
[2-Chloro-4-(3-{2-[(E)-3,5-diamino-6-chloro-pyrazine-2-carbonylimino}-1,3,8-triaza-spiro[4.5]dec-8-yl]-3-oxo-propyl)-phenoxy]-acetic acid 2-(2-oxo-piperidin-1-yl)-ethyl ester;
[4-(3-{2-[(E)-3,5-Diamino-6-chloro-pyrazine-2-carbonylimino]-1,3,8-triaza-spiro[4.5]dec-8-yl}-3-oxo-propyl)-phenoxy]-acetic acid 2-morpholin-4-yl-2-oxo-ethyl ester;
1-[(3-{2-[(E)-3,5-Diamino-6-chloro-pyrazine-2-carbonylimino]-1,3,8-triaza-spiro[4.5]decane-8-carbonyl}-benzenesulfonylamino)-methylycyclobutanecarboxylic acid dipropylcarbamoylmethyl ester;
3-[3-(3-{2-[(E)-3,5-Diamino-6-chloro-pyrazine-2-carbonylimino]-1,3,8-triaza-spiro[4.5]decane-8-carbonyl}-phenyl)-ureidoypropionic acid dipropylcarbamoylmethyl ester; and
1-[(3-{2-[(E)-3,5-Diamino-6-chloro-pyrazine-2-carbonylimino]-1,3,8-triaza-spiro[4.5]decane-8-carbonyl}-benzenesulfonylamino)-methyly]-cyclobutanecarboxylic acid 2-oxo-2-(2-trifluoromethyl-pyrrolidin-1-yl)-ethyl ester;
or a pharmaceutically acceptable salt thereof.

10. A pharmaceutical composition, comprising a compound according to claim 1, or a pharmaceutically acceptable salt thereof, and one or more pharmaceutically acceptable excipients, diluents and/or carriers.

11. A method for treating a cystic fibrosis or COPD, comprising:
administering an effective amount of a compound according to claim 1, or a pharmaceutically acceptable salt thereof, to a patient in need of such treatment.

12. The compound according to claim 1, wherein the compound is 3-(3-{2-[(E)-3,5-Diamino-6-chloro-pyrazine-2-carbonylimino]-1,3,8-triaza-spiro[4.5]decane-8-carbonyl}-benzenesulfonylamino)-propionic acid dipropylcarbamoylmethyl ester, or a pharmaceutically acceptable salt thereof.

13. The compound according to claim 12, wherein the compound is a succinate salt.

14. A method for treating cystic fibrosis, comprising:
administering an effective amount of a compound according to claim 12, or a pharmaceutically acceptable salt thereof, to a patient in need of such treatment.

15. The compound according to claim 1, wherein the compound is:
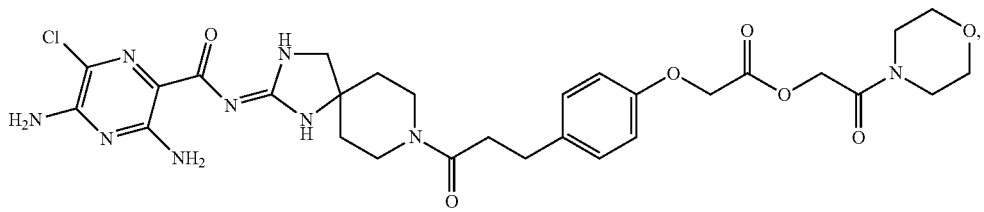 [SMILES: Nc1nc(N)c(C(=O)/N=C2\NCC3(CCN(C(=O)CCc4ccc(OCC(=O)OCC(=O)N5CCOCC5)cc4)CC3)N2)nc1Cl]
or a pharmaceutically acceptable salt thereof.
16. The compound according to claim 1, wherein the compound is:
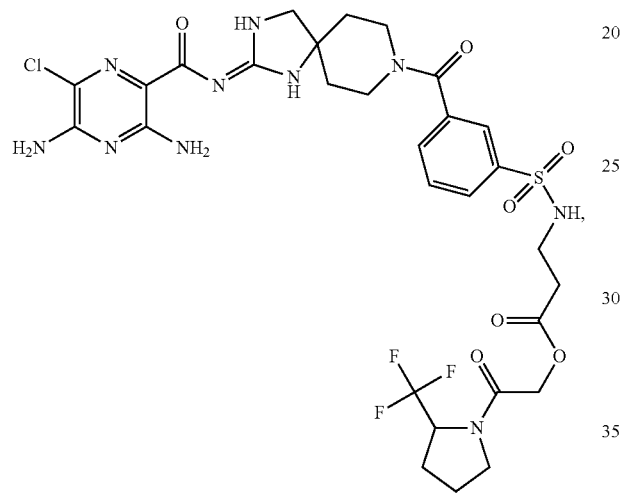
or a pharmaceutically acceptable salt thereof.
* * * * *